(12) United States Patent
Yoo et al.

(10) Patent No.: US 9,274,108 B2
(45) Date of Patent: Mar. 1, 2016

(54) SELF-ASSEMBLY OF MACROMOLECULES ON MULTILAYERED POLYMER SURFACES

(75) Inventors: Pil J. Yoo, Seoul (KR); Ki Tae Nam, Emeryville, CA (US); Jifa Qi, West Roxbury, MA (US); Soo-Kwan Lee, Seoul (KR); Juhyun Park, Daejeon (KR); Angela M. Belcher, Lexington, MA (US); Paula T. Hammond-Cunningham, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1102 days.

(21) Appl. No.: 12/278,390

(22) PCT Filed: Feb. 6, 2007

(86) PCT No.: PCT/US2007/002914
§ 371 (c)(1),
(2), (4) Date: Mar. 11, 2010

(87) PCT Pub. No.: WO2008/057127
PCT Pub. Date: May 15, 2008

(65) Prior Publication Data
US 2011/0114244 A1    May 19, 2011

Related U.S. Application Data

(60) Provisional application No. 60/765,773, filed on Feb. 6, 2006, provisional application No. 60/765,772, filed on Feb. 6, 2006.

(51) Int. Cl.
*C12N 7/00*      (2006.01)
*G01N 33/545*    (2006.01)

(52) U.S. Cl.
CPC ............ *G01N 33/545* (2013.01); *Y10T 156/10* (2015.01); *Y10T 428/273* (2015.01); *Y10T 428/31855* (2015.04); *Y10T 428/31971* (2015.04)

(58) Field of Classification Search
CPC ................................................ G01N 33/545
USPC ......... 423/6.7; 427/407.1; 435/174; 436/518, 436/531; 502/400–402
See application file for complete search history.

(56) References Cited

U.S. PATENT DOCUMENTS

| 5,223,409 A | 6/1993 | Ladner et al. |
| 5,403,484 A | 4/1995 | Ladner et al. |

(Continued)

FOREIGN PATENT DOCUMENTS

| EP | 1162459 A1 * | 12/2001 |
| EP | 1535952 A1 * | 6/2005 |

OTHER PUBLICATIONS

Lvov et al., Successive Deposition of Alternate Layers of Polyelectrolytes and a Charged Virus, 1994, Langmuir, vol. 10, pp. 4232-4236.*

(Continued)

*Primary Examiner* — Melanie Yu Brown
*Assistant Examiner* — Erik B Crawford
(74) *Attorney, Agent, or Firm* — Foley & Lardner LLP

(57) ABSTRACT

The invention is directed toward systems and methods for the formation of two dimensional monolayer structures of ordered biomacromolecules, such as viruses, atop cohesive polyelectrolyte multilayers to create functional thin films. Methods for the formation of such thin films are disclosed that involve an interdiffusion-induced assembly process of the biomacromolecules. The inventive systems provide a general platform for the systematic incorporation and assembly of organic, biological and inorganic materials and will enable many potential technological applications such as, for example, chemical and biological sensors, power devices and catalytic membranes.

29 Claims, 10 Drawing Sheets

(56) References Cited

U.S. PATENT DOCUMENTS

| | | | |
|---|---|---|---|
| 5,571,698 A | 11/1996 | Ladner et al. | |
| 5,766,905 A | 6/1998 | Studier et al. | |
| 5,885,808 A | 3/1999 | Spooner et al. | |
| 5,990,479 A | 11/1999 | Weiss et al. | |
| 6,207,392 B1 | 3/2001 | Weiss et al. | |
| 6,251,303 B1 | 6/2001 | Bawendi et al. | |
| 6,261,554 B1 | 7/2001 | Valerio et al. | |
| 6,274,323 B1 | 8/2001 | Bruchez et al. | |
| 6,306,610 B1 | 10/2001 | Bawendi et al. | |
| 6,319,426 B1 | 11/2001 | Bawendi et al. | |
| 6,322,901 B1 | 11/2001 | Bawendi et al. | |
| 6,326,144 B1 | 12/2001 | Bawendi et al. | |
| 6,423,551 B1 | 7/2002 | Weiss et al. | |
| 6,426,513 B1 | 7/2002 | Bawendi et al. | |
| 6,444,143 B2 | 9/2002 | Bawendi et al. | |
| 6,500,622 B2 | 12/2002 | Bruchez, Jr. et al. | |
| 6,576,291 B2 | 6/2003 | Bawendi et al. | |
| 6,649,138 B2 | 11/2003 | Adams et al. | |
| 6,815,064 B2 | 11/2004 | Treadway et al. | |
| 2001/0019820 A1 | 9/2001 | Li | |
| 2003/0068900 A1 | 4/2003 | Belcher et al. | |
| 2003/0073104 A1 | 4/2003 | Belcher et al. | |
| 2003/0113714 A1 | 6/2003 | Belcher et al. | |
| 2003/0148380 A1 | 8/2003 | Belcher | |
| 2004/0127640 A1 | 7/2004 | Belcher et al. | |
| 2004/0171139 A1 | 9/2004 | Belcher et al. | |
| 2005/0064508 A1 | 3/2005 | Belcher et al. | |
| 2005/0170336 A1* | 8/2005 | Belcher et al. | 435/5 |
| 2005/0180992 A1 | 8/2005 | Belcher et al. | |
| 2005/0221083 A1 | 10/2005 | Belcher et al. | |
| 2006/0121346 A1 | 6/2006 | Nam et al. | |

OTHER PUBLICATIONS

Yang et al., Self-assembled virus-membrane complexes, 2004, Nature Materials, vol. 3, pp. 615-619.*

Adams, M. et al., Entropically driven microphase transitions in mixtures of colloidal rods and spheres, Letters to Nature, 393:349-352 (1998).

Arico, A.S. et al., Nanostructured materials for advanced energy conversion and storage devices, Nature Materials, 4:366-377 (2005).

Armstrong, A.R. et al., Lithium-Ion Intercalation into $TiO_2$ Nanowires, Advanced Materials, 17(7):862-865 (2005).

Belcher, A.M. et al., Control of crystal phase switching and orientation by soluble mollusc-shell proteins, Nature, 281:56-58 (1996).

Borukhov, I. et al., Structural polymorphism of the cytoskeleton: A model of linker-assisted filament aggregation, Proceedings of the National Academy of Sciences of the United States of America, 102:3673-3678 (2005).

Brand, H.R. et al., Symmetry and Defects in the $C_M$ Phase of Polymeric Liquid Crystals, Macromolecules, 25:7223-7226 (1992).

Brown, S., Metal-recognition by repeating polypeptides, Nature Biotechnology, 15(3):269-272 (1997).

Caruso, F. et al., Nanoengineering of Inorganic and Hybrid Hollow Spheres by Colloidal Templating, Science, 282:1111-1114 (1998).

Cassagneau, T. and Fendler, J.H., Hight Density Rechargeable Lithium-Ion Batteries Self-Assembled from Graphite Oxide Nanoplatelets and Polyelectrolytes, Advanced Materials, 10(11):877-881 (1998).

Claye, A.S. et al., Solid-State Electrochemistry of the Li Single Wall Carbon Nanotube System, Journal of the Electrochemical Society, 147(8):2845-2852 (2000).

De Smedt, S.C. et al., Cationic polymer based gene delivery systems, Pharmaceutical Research, 17(2):113-126 (2000).

Decher, G. et al., Buildup of ultrathin multilayer films by a self-assembly process: III. Consecutively alternating adsorption of anionic and cationic polyelectrolytes on charged surfaces, Thin Solid Films, 210(211):831-835 (1992).

Decher, G., Fuzzy Nanoassemblies: Toward Layered Polymeric Multicomposites, Science, 277:1232-1237 (1997).

Delongchamp, D.M. and Hammond, P.T., Fast ion conduction in layer-by-layer polymer films, Chemistry of Materials, 15:1165-1173 (2003).

Dogic, Z. and Fraden, S., Smectic Phase in a Colloidal Suspension of Semiflexible Virus Particles, Physical Review Letters, 78:2417-2420 (1997).

Douglas, T. and Young, M., Host-guest encapsulation of materials by assembled virus protein cages, Nature, 393:152-155 (1998).

Flynn, C.E. et al., Viruses as vehicles for growth, organization and assembly of materials, Acta Materiala, 51(18):5867-5880 (2003).

Greenwood, J. et al., Regulation of filamentous bacteriophage length by modification of electrostatic interactions between coat protein and DNA, Journal of Molecular Biology, 217:223-227 (1991).

Hammond, P.T., Form and Function in Multilayer Assembly: New Applications at the Nanoscale, Advanced Materials, 16(15):1271-1293 (2004).

Herzfeld, J., Entropically-Driven Order in Crowded Solutions: from Liquid Crystals to Cell Biology, Accounts of Chemical Research, 29:31-37 (1996).

Huang, Y. et al., Programmable assembly of nanoarchitectures using genetically engineered viruses, Nano Letters, 5(7):1429-1434 (2005).

Joly, S. et al., Multilayer Nanoreactors for Metallic and Semiconduction Particles, Langmuir, 16(3):1354-1329 (2000).

Lavalle, P. et al., Comparison of the structure of polyelectrolyte multilayer films exhibiting a linear and exponential growth regime: an in situ atomic force microscopy study, Macromolecules, 35:4458-4465 (2002).

Lee, S.W. et al., Ordering of Quantum Dots Using Genetically Engineered Viruses, Science, 296:892-895 (2002).

Long, J.W. et al., Three-Dimensional Battery Architectures, Chemical Reviews, 104:4463-4492 (2004).

Mann, S. et al., Crystallization at Inorganic-organic Interfaces: Biominerals and Biomimetic Synthesis, Science, 261(5126):1286-1292 (1993).

Mao, C. et al., Viral assembly of oriented quantum dot nanowires, Proceedings of the National Academy of Sciences of the United States of America, 100(12):6946-6951 (2003).

Mao, C. et al., Virus-Based Toolkit for the Directed Synthesis of Magnetic and Semiconducting Nanowires, Science, 303:213-217 (2004).

Mui, S.C. et al., Block Copolymer-Templated Nanocomposite Electrodes for Rechargeable Lithium Batteries, Journal of the Electrochemical Society, 149(2):A1610-A1615 (2002).

Murr, M.M. and Morse, D.E., Fractal intermediates in the self-assembly of silicatein filaments, Proceedings of the National Academy of Sciences of the United States of America, 102(33):11657-11662 (2005).

Mészáros, R. et al., Adsorption and electrokinetic properties of polyethyelenimine on silica surfaces, Langmuir, 18:6164-6169 (2002).

Nam, K.T. et al., Genetically Driven Assembly of Nanorings Based on M13 Virus, Nano Letters, 4(1):23-27 (2003).

Nam, K.T. et al., Virus-Enabled Synthesis and Assembly of Nanowires for Lithium Ion Battery Electrodes, Science, 312(5775):885-888 (2006).

Peelle, B.R. et al., Design Criteria for Engineering Inorganic Material-Specific Peptides, Langmuir, 21(15):6929-6933 (2005).

Peyratout, C.S. and Dähne, L., Tailor-Made Polyelectrolyte Microcapsules: From Multilayers to Smart Containers, Angewandte Chemie International Edition England, 43:3762-3783 (2004).

Picart, C. et al., Molecular basis for the explanation of the exponential growth of polyelectrolyte multilayers, Proceedings of the National Academy of Sciences of the United States of America, 99(20):12531-12535 (2002).

Purdy, K.R. and Fraden, S., Isotropic-cholesteric phase transition of filamentous virus suspensions as a function of rod length and charge, Physical Review, E70:061703-061708 (2004).

Russell, T.P. et al., Direct observation of reptation at polymer interfaces, Letters to Nature, 365:235-237 (1993).

(56) References Cited

OTHER PUBLICATIONS

Rädler, J.O. et al., Structure of DNA-Cationic Liposome Complexes: DNA Intercalation in Multilamellar Membranes in Distinct Interhelical Packing Regimes, Science, 275:810-814 (1997).

Sakamoto, J.S. and Dunn, B., Vanadium Oxide-Carbon Nanotube Composite Electrodes for Use in Secondary Lithium Batteries, Journal of Electrochemical Society, 149(1):A26-A30 (2002).

Seeman, N.C., DNA in a material world, Nature, 421(6921):427-431 (2003).

Tang, Z. et al., Nanostructured artificial nacre, Nature Materials, 2:413-418 (2003).

Warner, M.G. and Hutchison, J.E., Linear assemblies of nanoparticles electrostatically organized on DNA scaffolds, 2:272-277 (2003).

Whaley, S.R. et al., Selection of peptides with semiconductor binding specificity for directed nanocrystal assembly, Nature, 405(6787):665-668 (2000).

Whang, D. et al., Large-Scale Hierarchial Organizations of Nanowire Arrays of Integrated Nanosystems, Nano Letters, 3(9):1255-1259 (2003).

Yang, P., Nanotechnology: wires on water, Nature, 425(6955):243-244 (2003).

Yoo, P.J. et al., Spontaneous assembly of viruses on multilayered polymer surfaces, Nature Materials, 5:234-240 (2006).

Zhang, S., Fabrication of novel biomaterials through molecular self-assembly, Nature Biotechnology, 21(10):1171-1178 (2003).

Zimmermann, K. et al., The iconic properties of the filamentous bacteriophages $Pf_1$ and fd., The Journal of Biological Chemistry, 261:1653-1655 (1986).

\* cited by examiner

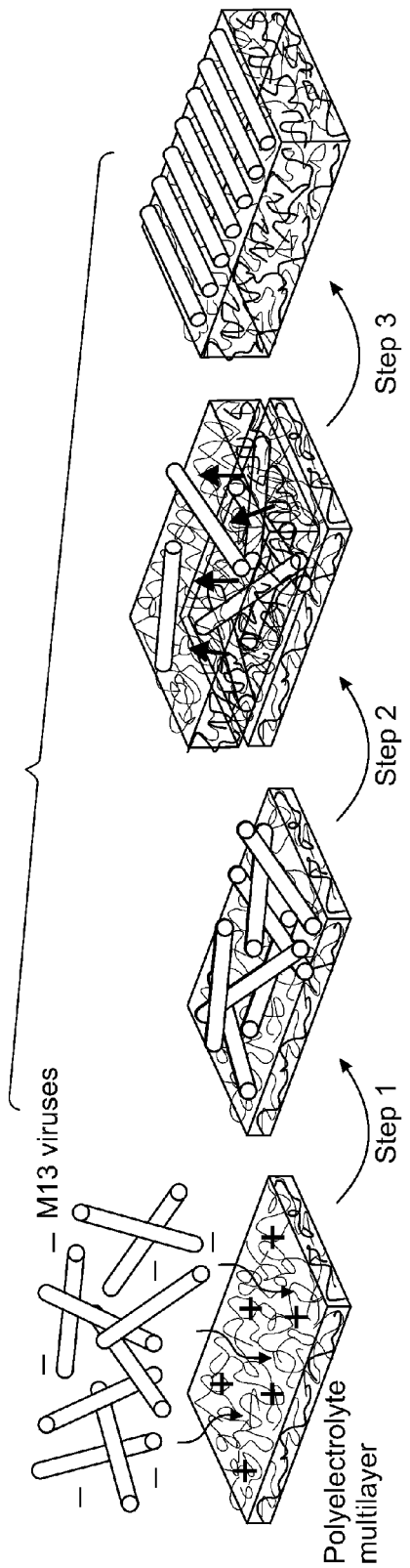
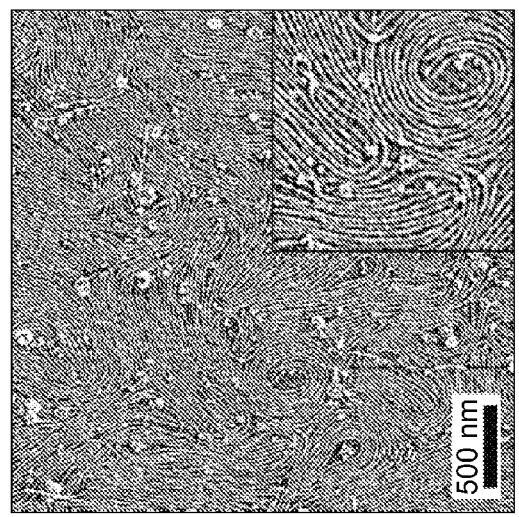
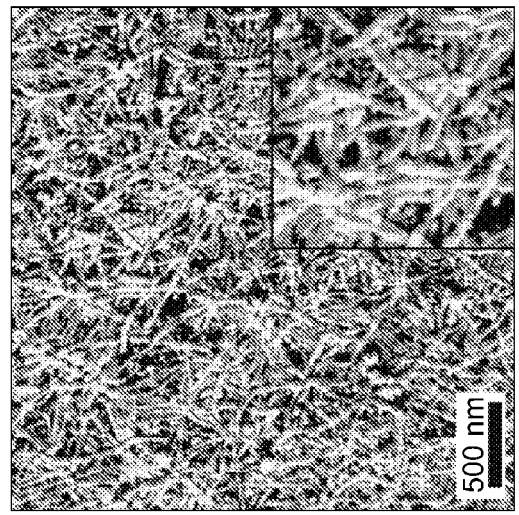
FIG. 2a
FIG. 2c
FIG. 2b

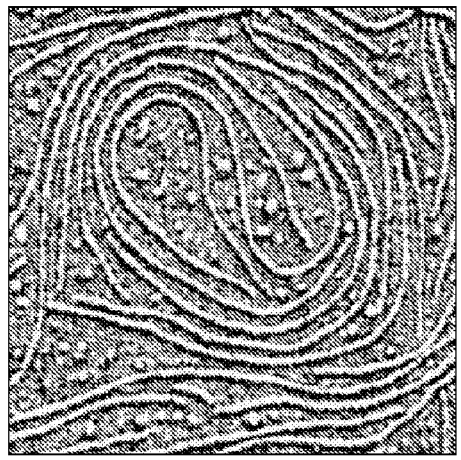
FIG. 4d
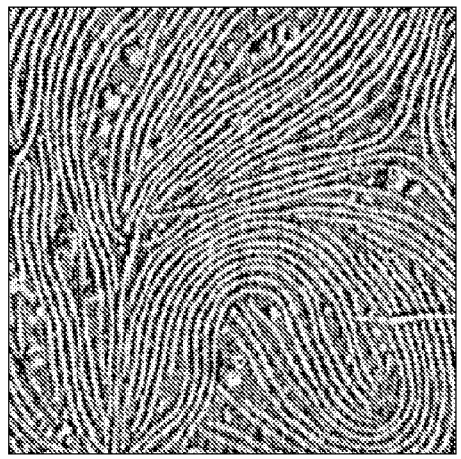
FIG. 4c
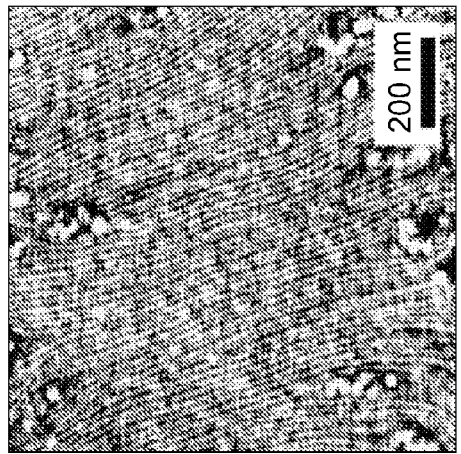
FIG. 4b
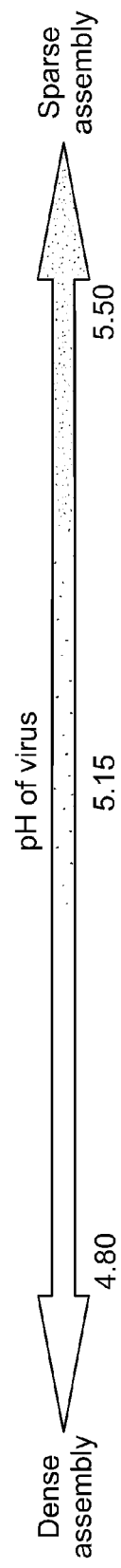

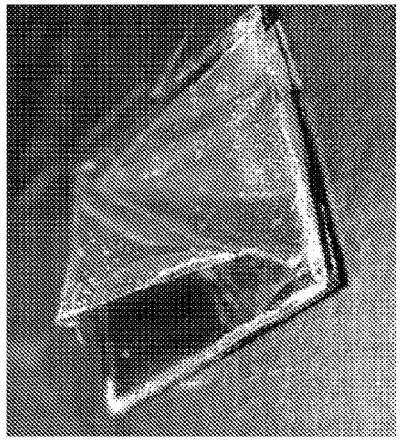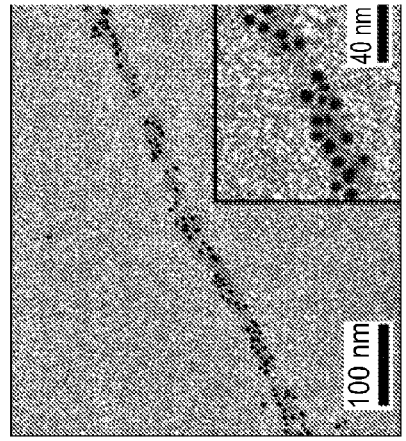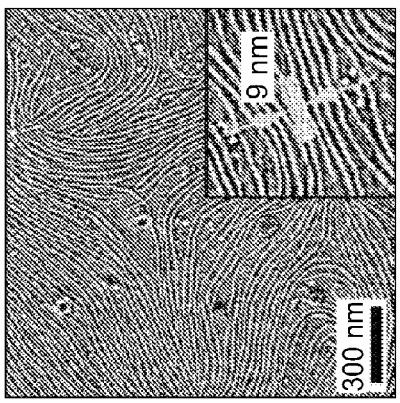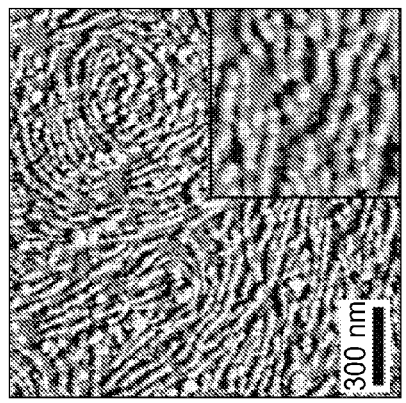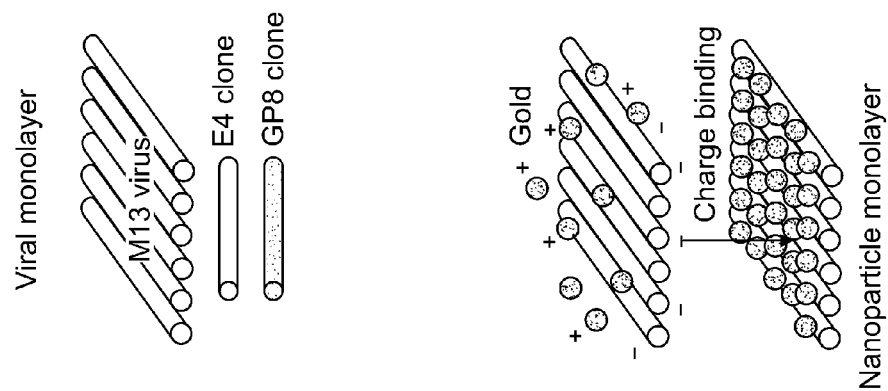
FIG. 5a
FIG. 5b

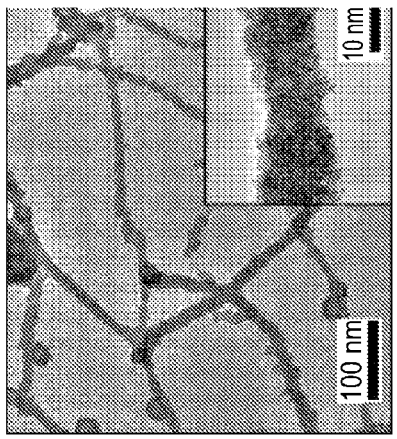
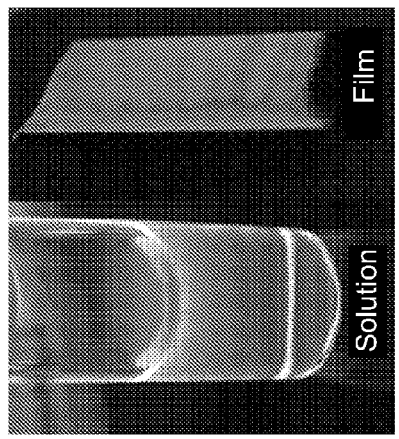
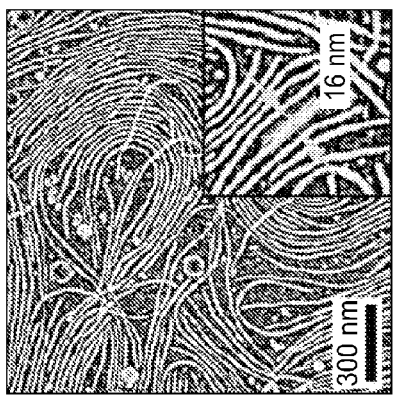
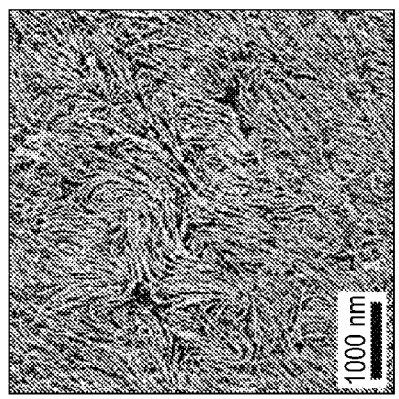
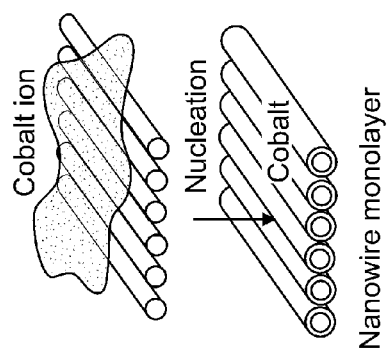
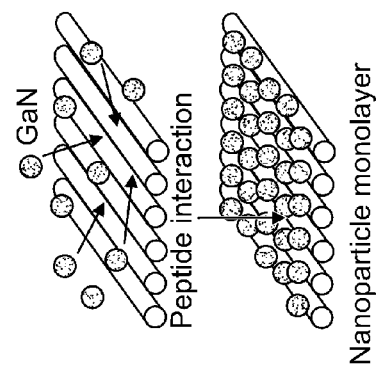
FIG. 5c
FIG. 5d

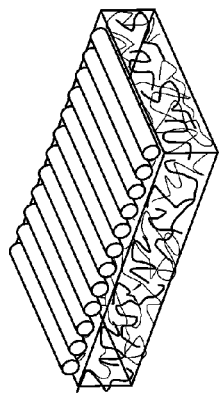
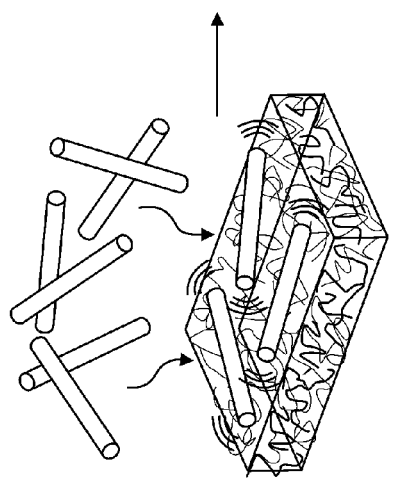
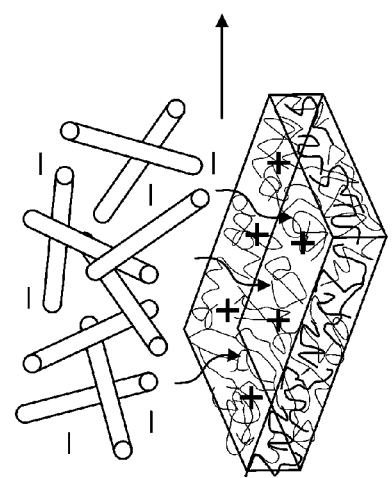
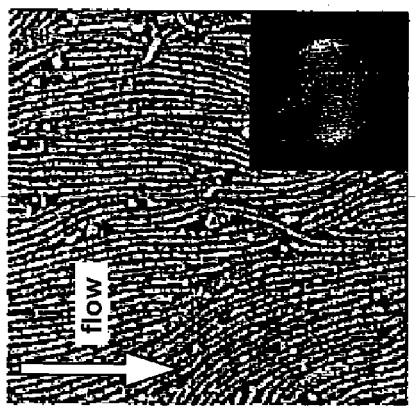
FIG. 8c
FIG. 8b
FIG. 8a
FIG. 9b
FIG. 9a

SELF-ASSEMBLY OF MACROMOLECULES ON MULTILAYERED POLYMER SURFACES

RELATED APPLICATIONS

This application is a National Stage Entry of International Application No. PCT/US2007/002914 filed on Feb. 6, 2007 and entitled "Self-Assembly of Macromolecules on Multilayered Polymer Surfaces" (incorporated herein by reference in its entirety), and claims priority from Provisional Application No. 60/765,773 filed on Feb. 6, 2006 and entitled "Spontaneous Assembly of Viruses on Multilayered Polymer Surfaces", and from Provisional Application No. 60/765,772 filed on Feb. 6, 2006 and entitled "Fabrication of Electrostatically Mediated and Self-Assembled Monolayer of Macromolecules on Mobility-Enhancing Polyelectrolyte Multiplayer". Each of the provisional applications is incorporated herein by reference in its entirety.

GOVERNMENT INTERESTS

This invention was made with government support under grant number DAAD19-02-D-0002 awarded by the Army Research Office. The United States government may have certain rights in the invention.

BACKGROUND OF THE INVENTION

A significant prerequisite in nano-involved and bio-inspired approaches for the fabrication of electrical and optical devices or organization of building blocks to hierarchical structures, is the construction of well-ordered two-dimensional monolayers. It plays a key role not only in embedding a specific functionality on the focused area but also stacking to a multicomponent layer for further higher dimensional integration. Effects to date have primarily focused on two main methods: self-assembly monolayer (SAM) and Langmuir-Blodgett monolayer (LBM).

The self-assembly monolayer technique is based on the formation of covalent or coordination bonding between assemblable species and surface. It can generate dense and stable monolayers and serve as a template for bottom-up based nano-assembly. Due to the requirement of specific binding, however, the range of material applicability is limited to some chemical species, such as those amenable to thiol or silane chemistry. The Langmuir-Blodgett monolayer technique utilizes the hydrophobic-hydrophilic interactions at the interface between specific molecules and water surface. In this technique, molecules are spread to form a monolayer over the water surface and then transferred to the other processible solid surface. By varying an external force to guide the monolayer spreading, molecular density and orientation can be tuned as desired. In spite of these advantages of controllability in film properties, LBM has shown some drawbacks typically in film processiblity and stability due to the use of fluidic and unstable water surface.

Electrostatic interaction has been one of the important driving forces for molecular self-assembly. The most widely accepted technique is layer-by-layer (LBL) assembly. The technique takes advantage of electrostatic attractive forces between charged polymers and oppositely-charged surfaces, and film growth is typically achieved stepwise by the repetitive exposure of substrate to dilute polycation and polyanion solutions. Using this approach it is possible to control film thickness on the nanometer scale by simply increasing the number of adsorbed polycation/polyanion layers, or to fabricate films possessing gradients of different polyelectrolyte components by manipulating the sequences in which multiple different polymer components are adsorbed (G. Decher, Science, 1997, 277: 1232-1237; F. Caruso et al., Science, 1998, 282: 1111-1114; Z. Tang et al., Nature Mater., 2003, 2: 413-418; C. S. Peyratout and L. Dahne, Angew. Chem. Int. Ed. Engl., 2004, 43: 3762-3783). This assembly process has the added advantage of strong compatibility with biomolecular species without loss of biological function. Thus, LBL assembly has a wide variety of potential applications, including surface modification, sensors, conducting or light-emitting devices, drug delivery, nano-reactors, etc.

However, the formation mechanism, internal structure, and molecular properties of LBL-produced polyelectrolyte multilayers are still poorly understood, and this has hindered taking full advantage of this powerful technique.

SUMMARY OF THE INVENTION

The present invention is directed to new systems and strategies for the construction of quantitatively scalable and functionally controllable biomolecular surfaces on a polyelectrolyte multilayer film. In particular, the present invention encompasses the recognition that while the idea that randomly arranged supermolecular species incorporated in a network medium can ultimately create ordered structures at the surface may be counterintuitive, such order can be accommodated by regulating dynamic and equilibrium driving forces. More specifically, the present Applicants have demonstrated the ordering of genetically engineered M13 virus particles, highly complex biomacromolecules, atop a cohesive polyelectrolyte multilayer (PEM) thin film. In conventional polyelectrolyte multilayer (PEM) systems, strong charge binding between ion pairs yields an ionically crosslinked network in which the mobility of polymer chains is significantly limited; in some cases, the intermixing or diffusion of polyions (C. Picard et al., Proc. Natl. Acad. Sci. USA, 2002, 99: 12531-12535) within the interior of the PEM film during multilayer construction is not facilitated. Adsorption of a charged virus monolayer within such a system would only generate irreversible monolayer charge binding and lead to a randomly stacked virus layer (see, for example, FIG. 2b). The present Applicants have shown that when one of the polyelectrolytes is able to interdiffuse into the multilayer, it is, however, possible to "unlock" these electrostatic crosslinks through competitive interactions. Thus, in this case, the competitive interdiffusion that usually leads to disorder and disruption in electrostatically assembled thin films is harnessed to achieve spontaneous ordering of virus particles during the assembly process.

Accordingly, the present invention provides a new synergistic route for monolayer formation of charged biomacromolecules, which combines the advantages of self-assembly monolayer (SAM) and Langmuir-Blodgett monolayer (LBM) methods, by mediating the electrostatic interactions between polyelectrolytes and the biomacromolecule, allowing the control of assembly density and directionality while maintaining the film stability and functionality. The film thickness can be varied from a few nanometers to tens of micrometers. In addition, the polyelectrolyte multilayer film can be doped with a broad range of materials, from conducting and redox-active polymers to biologically compatible materials. The flexibility, variety of organic, biological or inorganic materials that can grow on the surface of these films and the low cost of synthesis and assembly of the inventive materials systems will enable many potential technological applications, including, but not limited to, chemical and biological sensors, power devices and catalytic reactive membranes.

More specifically, the present invention provides a composition comprising a plurality of biomacromolecules; and a polyelectrolyte multilayer film, wherein the polyelectrolyte multilayer film comprising a positively-charged polyelectrolyte and a negatively-charged polyelectrolyte, wherein the plurality of biomacromolecules form a two-dimensional monolayer on the surface of the polyelectrolyte multilayer film.

The biomacromolecules may be all identical or, alternatively, the plurality of biomacromolecules may comprise different biomacromolecules. Biomacromolecules may be selected from the group consisting of proteins, polynucleotides, lipids, polysaccharides, and viruses.

In certain embodiments, the plurality of biomacromolecules comprises a virus. In some embodiments, the virus is a filamentous virus. In some embodiments, the virus is a bacteriophage virus. In some embodiments, the virus is a helical virus. In some embodiments, the virus is a rod-shaped virus, for example, a rigid rod-shaped virus. Preferred rod-shapes viruses have a cross-sectional diameter of about 3 nm to about 20 nm and a length of about 60 nm to about 6,000 nm.

In certain embodiments, the virus comprises at least one recognition site capable of a selective binding to or nucleating of a conjugate moiety. In some embodiments, the virus comprises more than one recognition site. For example, the virus may comprise a first recognition site capable of a first selective binding to or nucleating of a first conjugate moiety, a second recognition site located differently from the first recognition site capable of a second selective binding to or nucleating of a second conjugate moiety, and optionally, a third recognition site located differently from the first and second recognition sites capable of a third selective binding to or nucleating of a third conjugate moiety.

The virus may be genetically engineered to comprise one or more of these recognition sites. In certain embodiments, a recognition site comprises an expressed protein, peptide or peptide oligomer.

In certain embodiments, the virus comprises at least one recognition site capable of a selective binding to or nucleating of a conjugate moiety that is a member of the group consisting of an inorganic material, an organic material, and a biomolecular material. For example, the conjugate moiety may comprise a semiconductor, metallic, magnetic, polymeric, particulate, nanoparticulate, single crystalline, polycrystalline, amorphous, electronically conducting, optically active, conducting polymeric, light-emitting, phosphorescent, fluorescent, glass or ceramic moiety.

In certain compositions of the present invention, the plurality of biomacromolecules form a dense, ordered two-dimensional monolayer of biomacromolecules on the surface of the polyelectrolyte multilayer film. In other compositions of the present invention, the plurality of biomacromolecules form a sparse two-dimensional monolayer of biomacromolecules. The monolayer of biomacromolecules may have a density of about 1 to about 100 biomacromolecules/$\mu m^2$.

In certain preferred embodiments, the polyelectrolyte film is produced by layer-by-layer assembly.

In some embodiments, the positively-charged polyelectrolyte is a weak positively-charged polyelectrolyte. In some embodiments, the negatively-charged polyelectrolyte is a weak negatively-charged polyelectrolyte. In some embodiments, the positively-charged polyelectrolyte is a weak positively-charged polyelectrolyte and the negatively-charged polyelectrolyte is a weak negatively-charged polyelectrolyte, and they form a pair of weak oppositely charged polyelectrolytes. The pair of weak oppositely charged polyelectrolytes may be a member of the group consisting of linear polyethyleneimine/poly(styrenesulfonic acid) (LPEI/SPS), poly(diallyldimethyl-ammonium chloride)/poly(styrenesulfonic acid) (PDAC/SPS), poly(allylamine hydrochloride/poly(styrenesulfonic acid) (PAH/SPS), linear polyethyleneimine/ poly-(acrylic acid) (LPEI/PAA), poly(diallyldimethylammonium chloride)/poly(acrylic acid) (PDAC/PAA), and poly (styrenesulfonic acid)/poly(acrylic acid) (PAH/PAA). In certain embodiments, the pair of oppositely charged polyelectrolytes is linear polyethyleneimine/poly-(acrylic acid) (LPEI/PAA).

In certain embodiments, the pair of oppositely charged polyelectrolytes exhibits a superlinear thickness growth.

In certain embodiments, the polyelectrolytes have a surface charge density that is higher than the surface charge density of the biomacromolecules. For example, the surface charge density of the polyelectrolytes can be at least about 2 fold higher, at least about 3 fold higher, at least about 4 fold higher, or more than 4 fold higher than the surface charge density of the biomacromolecules.

In some embodiments, the positively-charged polyelectrolyte and/or the negatively-charged polyelectrolyte is/are biocompatible. In some embodiments, the positively-charged polyelectrolyte and/or the negatively-charged polyelectrolyte is/are degradable (e.g., biodegradable).

In another aspect, the present invention provides a film comprising any of the compositions disclosed herein. The film may have a thickness between about 10 m and about 1000 μm.

In still another aspect, the present invention provides a device comprising an inventive film. The device can be an electronic device, an optoelectronic device, an electrochemical device, or an electromechanical device. For example, the device may be a sensor, a conductive system, a power device, or a catalytic membrane.

In yet another aspect, the present invention provides methods for preparing compositions disclosed herein.

A first method comprises steps of: providing a plurality of negatively-charged biomacromolecules; providing a polyelectrolyte multilayer thin film produced by layer-by-layer assembly using a weak positively-charged polyelectrolyte and a weak negatively-charged polyelectrolyte, wherein the surface of the film is positively charged; contacting the surface of the film with the biomacromolecules to obtain a thin film comprising biomacromolecules electrostatically bound to its surface; and forming, on top of the obtained thin film, a second polyelectrolyte multilayer by layer-by-layer assembly using the weak positively-charged polyelectrolyte and the weak negatively-charged polyelectrolyte.

In certain embodiments, the polyelectrolyte multilayer thin film has a thickness of less than about 50 nm. In some embodiments, the polyelectrolyte multilayer thin film comprises less than about 6 bilayers.

A second method comprises steps of: providing a plurality of negatively-charged biomacromolecules; providing a polyelectrolyte multilayer film produced by layer-by-layer assembly using a weak positively-charged polyelectrolyte and a weak negatively-charged polyelectrolyte, wherein the film is thick and the surface of the film is positively charged; and contacting the surface of the film with biomacromolecules.

In certain embodiments, the polyelectrolyte multilayer thick film has a thickness of more than about 50 nm. In some embodiments, the polyelectrolyte multilayer thick film comprises more than about 6 bilayers.

In these methods of preparation, the biomacromolecules and polyelectrolytes can be as described above.

In the inventive methods of preparation, the step of providing a plurality of biomacromolecules comprises providing an aqueous solution comprising the plurality of biomacromolecules. In certain embodiments, the aqueous solution of biomacromolecules has a pH that is selected such that strong repulsion takes place between the negatively-charged biomacromolecules. In other embodiments, the aqueous solution of biomacromolecules has a pH that is selected such that weak repulsion takes place between the negatively-charged biomacromolecules.

In certain embodiments, the step of contacting the surface of the film with the biomacromolecules may comprise depositing the aqueous solution of biomacromolecules on the film surface. In other embodiments, the step of contacting the surface of the film with the biomacromolecules may comprise flowing the aqueous solution of biomacromolecules in the microfluidic channel onto the film surface.

These and other objects, advantages and features of the present invention will become apparent to those of ordinary skill in the art having read the following detailed description of the preferred embodiments.

BRIEF DESCRIPTION OF THE DRAWING

FIG. 2 shows a schematic strategy for viral monolayer assembly according to an embodiment of the present invention and an AFM demonstration of the disordered state and the ordered state of the M13 virus. FIG. 2(a) is a schematic presentation of an embodiment of an inventive procedure for monolayer assembly of M13 virus on a thin film of polyelectrolyte multilayer LPEI/PAA (see Example 1). FIG. 2(b) shows a phase-mode AFM image of the randomly stacked and aggregated structure of M13 viruses on 5.5 bilayers of strong PEM of polydiallylamine hydrochloride and polystyrene sulfonate. FIG. 2(c) shows a phase-mode AFM image of a closely packed monolayer of M13 virus on weak PEM (deposited at pH 5.0) of LPEI and PAA. Viruses were initially adsorbed on 4.5 bilayers of LPEI/PAA (hereafter, it will be denoted as $(LPEI/PAA)_n$, where n is a deposition number) under the same pH conditions, then additional $(LPEI/PPA)_{5.5}$ layers were deposited onto the virus and promoted the ordering of the virus. The images in b and c are of size $3 \times 3$ $\mu m^2$ (the inset illustrates the magnified image of size $800 \times 800$ $nm^2$) and the Z-range (relative phase shift scale) is $30°$.

FIG. 5 shows results that demonstrate templated biomineralization on the virus monolayer (see Example 1). The size of phase-mode AFM images in a-c is $1.5 \times 1.5$ $\mu m^2$ and the Z-range is $30°$ (the inset shows the magnified image of size $400 \times 400$ $nm^2$). a, An assembled virus monolayer template for growing materials. Viruses are assembled at pH 5.1 on a $(LPEI/PAA)_{100.5}$ flexible free-standing film. AFM image (left) and photograph (right, sample size 2 cm×4 cm). b, AFM and transmission electron microscope (TEM) images of gold nanoparticles attached to the virus monolayer. 5-nm cationic gold particles were incubated on negatively charged M13 virus. The inset shows the alignment of particles along the M13 virus. Gold-attached viruses were collected for TEM imaging by dissolving the substrate polymer layer. c, AFM and TEM images of cobalt-nucleated virus nanowires. The nucleation of cobalt increased contrast in the phase-mode AFM image. The inset AFM image shows that the cobalt-coated virus is about 16 nm in width, which is nearly two times the width of virus in a. d, AFM ($5 \times 5$ $\mu m^2$) and fluorescence images of the GaN virus nanowire films.

FIG. 8 is a schematic presentation of an embodiment of an inventive procedure for monolayer assembly of M13 virus on a thick film of polyelectrolyte multilayer LPEI/PAA.

FIG. 9a shows a microfluidic channel for directionality and FIG. 9b shows an AFM image of one dimensionally ordered virus monolayer ($1.5 \times 15$ $\mu m^2$).

DEFINITIONS

Figure 1A:
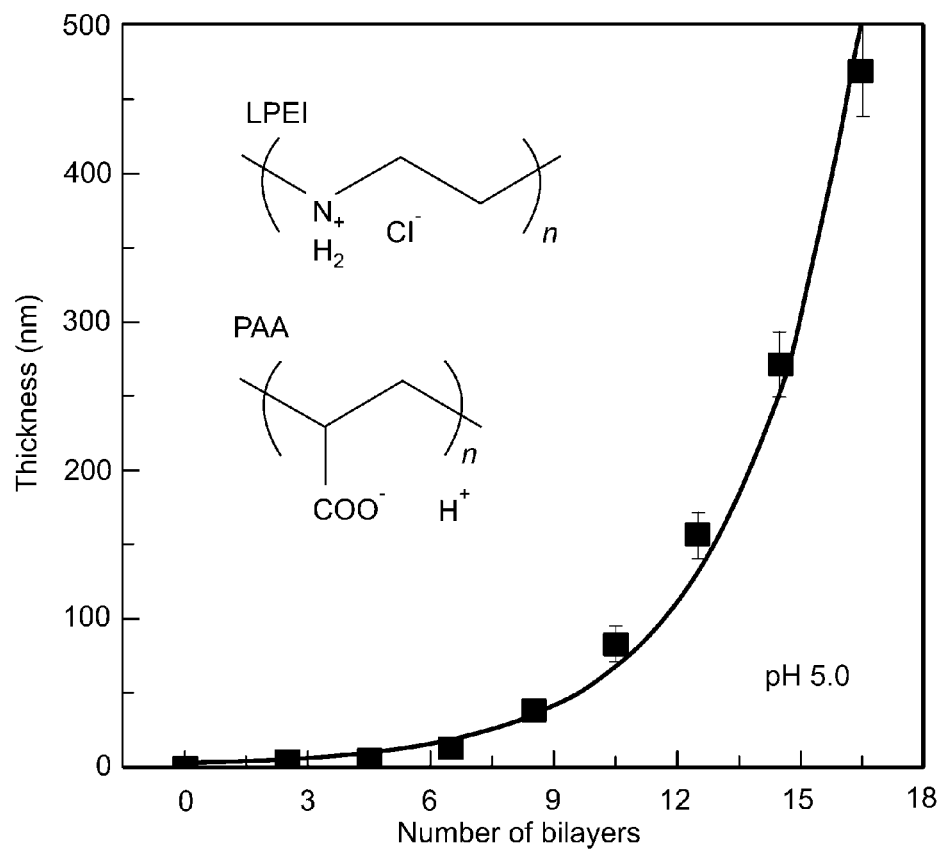
FIG. 1(a) presents a sketch of superlinear thickness growth in an LPEI/PAA LBL-assembled film at pH 5.0 (see Example 1). The solid line is an exponentially fit curve and error bars indicate standard deviations.

Unless otherwise stated, all technical and scientific terms used herein have the meaning commonly understood by a person skilled in the art to which this invention belongs. The following terms have the meaning ascribed to them unless specified otherwise.

As used herein, the term "biocompatible" is intended to describe any material which does not elicit a substantial detrimental response in vivo.

The term "biodegradable", when used to characterize a material (e.g., a polymer), refers to a material that degrades under physiological conditions to form a product that can be metabolized or excreted without damage, or without permanent damage, to a subject (e.g., a human patient). Biodegradable materials may be hydrolytically degradable, may require cellular and/or enzymatic action to fully degrade, or both. Biodegradable materials also include materials that are broken down within cells. Degradation may occur by hydrolysis, enzymatic processes, phagocytosis, or other processes. Biodegradable materials also include materials that are degraded by body heat.

The term "bioactive agent" and "biologically active agent" are used herein interchangeably. They refer to compounds or entities that alter, inhibit, activate or otherwise affect biological or chemical events. For example, bioactive agents may include, but are not limited to, anti-AIDS substances, anti-cancer substances, antibiotics, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anticoagulants and/or antithrombotic agents, local anesthetics, ophthalmics, prostaglandins, anti-depressants, anti-psychotic substances, anti-emetics, and imaging agents. The bioactive agent may be a drug.

As used herein, the term "biomolecules" refers to molecules (e.g., proteins, amino acids, peptides, polynucleotides, nucleotides, carbohydrates, sugars, lipids, nucleoproteins, glycoproteins, lipoproteins, steroids, etc) whether naturally-occurring or artificially created (e.g., by synthetic or recombinant methods) that are commonly found in cells and tissues. Specific classes of biomolecules include, but are not limited to, enzymes, receptors, neurotransmitters, hormones, cytokines, cell response modifiers such as growth factor and chemotactic factors, antibodies, vaccines, haptens, toxins, interferons, ribozymes, anti-sense agents, plasmids, DNA and RNA.

As used herein, the term "biomacromolecules" refers to biomolecules that have a high molecular weight. The molecular weight of a biomacromolecule may be anywhere from about 1,000 to about 100,000,000 grams/mole, preferably from about 10,000 to about 25,000,000 grams/mole.

The term "degradation", as used herein in reference to a polymer, relates to the cleavage of a covalent polymer backbone. Full degradation of a polymer breaks the polymer down to monomeric species. Degradation of a polymer may occur by a variety of mechanisms including, but not limited to, hydrolytic degradation, biodegradation, thermal degradation, photolytic degradation, and any combination thereof.

As used herein, the term "electrolyte" refers to any chemical compound that dissociates in aqueous solutions, and becomes charged. The terms "polyelectrolyte" and "polyion" are used herein interchangeably and refer to a polymer whose repeating units bear an electrolyte group which dissociates in aqueous solutions, making the polymer charged. If after dissolution in an aqueous solution the resulting polyelectrolyte is positive, it is referred to as a polycation or a positively charged polyelectrolyte. Conversely, if the resulting polyelectrolyte is negative, it is referred to as a polyanion or a negatively charged polyelectrolyte. Polyelectrolytes can be naturally-occurring or synthetic polymers. Polyelectrolytes are classified as either "weak polyelectrolytes" or "strong polyelectrolytes". A strong polyelectrolyte is one which dissociates completely in aqueous solutions of neutral pHs (i.e., about pH 7). A weak polyelectrolyte, by contrast, has a dissociation constant ($pK_a$) in the range of about 2 to about 10, meaning that it will be partially dissociated at intermediate (i.e., neutral) pH. Thus, weak polyelectrolytes are not fully charged in solution, and moreover their fractional charge can be modified by changing the solution pH.

The term "physiological conditions", as used herein, relates to the range of chemical (e.g., pH, ionic strength) and biochemical (e.g., enzyme concentrations) conditions likely to be encountered in the intracellular and extracellular fluids or tissues. For most fluids and tissues, the physiological pH ranges from about 7.0 to about 7.4.

The terms "polynucleotide", "nucleic acid" and "oligonucleotide" are used herein interchangeably, and refer to a polymer of nucleotides. Typically, a polynucleotide comprises at least three nucleotides. DNAs and DNAs are polynucleotides. A polynucleotide may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propylnyluridine, C5-bromouridine, C5-fluorouridine, C5-iodouridine, C5-methyl-cytidine, 7-deazaadenosine, 7-deazaguanosine, 8-oxoadenosine, 8-oxoguanosine, O(6)-methylguanine, and 2-thiocytidine), biologically modified bases (e.g., methylated bases), intercalated bases, and modified sugars (e.g. phosphorothioates and 5'-N-phosphoramidite linkages). The polymer may also be a short strand of nucleic acids such as RNAi, siRNA, or shRNA.

The terms "polypeptide", "peptide" and "protein" are used herein interchangeably. They refer to a string of at least three amino acids linked together by peptide bonds. "Peptide" may refer to an individual peptide or a collection of peptides. Peptides may contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids of a peptide may be modified, for example, by addition of a chemical entity such as a carbohydrate group, a phosphate group, a farnesyl group, an isofarnesyl group, a fatty acid group, a linker for conjugation, functionalization, or other modification, etc. Modifications of a peptide may be introduced to produce a more stable peptide. These modifications may include cyclization of the peptide, the incorporation of D-amino acids, etc. Preferably, none of the modifications should substantially interfere with the desired activity of the peptide.

The terms "polysaccharide" and "oligosaccharide" are used herein interchangeably. They refer to a polymer or oligomer of carbohydrate residues. The polymer or oligomer may consist of anywhere from two to hundreds to thousands of sugar units or more. The term "carbohydrate" generally refers to a relatively low molecular weight polymer, while "polysaccharide" typically refers to a higher molecular weight polymer. Polysaccharides may be purified from natural sources such as plants or may be synthesized de novo in the laboratory. Polysaccharides isolated from natural sources may be modified chemically to change their chemical or physical properties (e.g., reduced, oxidized, phosphorylated, cross-linked). Carbohydrate polymers or oligomers may include natural sugars (e.g., glucose, fructose, galactose, mannose, arabinose, ribose, xylose, etc.) and/or modified sugars (e.g., 2'-fluororibose, 2'-deoxyribose, etc.). Polysaccharides may also be either straight or branched. They may contain both natural and/or unnatural carbohydrate residues. The linkage between the residues may be the typical ether linkage found in nature or may be a linkage only available to synthetic chemists. Examples of polysaccharides include cellulose, maltin, maltose, starch, modified starch, dextran, poly (dextrose), and fructose. Glycosaminoglycans are also considered polysaccharides. Sugar alcohol, as used herein, refers to any polyol such as sorbitol, mannitol, xylitol, galactitol, erythritol, inositol, ribitol, dulcitol, adonitol, arabitol, dithio-erythritol, dithiothreitol, glycerol, isomalt, and hydrogenated starch hydrolysates.

The term "small molecule", as used herein, refers to molecules, whether naturally-occurring or artificially created (e.g., via chemical synthesis) that have a relatively low molecular weight. Typically, small molecules are monomeric and have a molecular weight of less than about 1500 Da. A small molecule may be a biologically active agent.

DETAILED DESCRIPTION OF CERTAIN PREFERRED EMBODIMENTS

I—Introduction

As mentioned above, the present invention provides new systems and methods for the formation of two dimensional monolayer structures of ordered biomacromolecules (e.g., viruses such as M13 virus systems) atop cohesive polyelectrolyte multilayers to create functional or multifunctional thin films. In addition to being simple, rapid, low cost, efficient and environment friendly, the inventive methods allow the control of assembly density and directionality while maintaining the film stability and functionality. The inventive systems provide a general platform for the systematic incorporation and assembly of organic, biological and inorganic materials.

Certain aspects of preferred embodiments of the invention are described below in more detail. Those of ordinary skill in the art will appreciate that a variety of embodiments or versions of the invention are not specifically discussed but are nonetheless within the scope of the present invention, as defined by the appended claims.

In the present invention, reference can be made to Nam et al., Nano Lett., 2003, 4: 23-27; Yoo et al., Nature Mater., 2006, 5: 234-240; Provisional Application No. 60/765,773 entitled "Spontaneous Assembly of Viruses on Multilayered Polymer Surfaces", to A. Belcher; and Provisional Application No. 60/765,772 entitled "Fabrication of Electrostatically Mediated and Self-Assembled Monolayer of Macromolecules on Mobility-Enhancing Polyelectrolyte Multiplayer" to A. Belcher, which are incorporated herein by reference in their entirety.

In practice of the present invention, reference can also be made to the article, C. E. Flynn et al., Acta Materiala, 2003, 51: 5867-5880 entitled "Viruses as vehicles for growth, organization, and assembly of materials". This reference, as well as all references cited in this article are incorporated herein by reference in their entirety.

In addition, one skilled in the art can also refer to the following patent literature for selection of virus, genetic engineering methods, and for materials to be used with genetically engineered viruses; phage display libraries and experimental methods for using them in biopanning are further described, for example, in the following U.S. published patent applications to Belcher et al.: Applications (1) No. 2003-0068900 entitled "Biological Control of Nanoparticle Nucleation, Shape, and Crystal Phase", published Apr. 10, 2003; (2) No. 2003-0073104 entitled "Nanoscale Ordering of Hybrid Materials Using Genetically Engineered Mesoscale Virus", published Apr. 17, 2003; (3) No. 2003-0113714 entitled "Biological Control of Nanoparticles", published Jun. 19, 2003; (4) No. 2003-0148380 entitled "Molecular Recognition of Materials", published Aug. 7, 1003; (5) No. 2004-0127640 entitled "Composition, method, and use of bifunctional biomaterials", published Sep. 4, 2003; (6) No. 2005-0064508 entitled "Peptide Mediated Synthesis of Metallic and Magnetic Materials", published Mar. 24, 2005; (7) No. 2004-0171139 entitled "Fabricated BioFilm Storage Device", published Sep. 2, 2004; (8) No. 2005-0170336 entitled "Multifunctional Biomaterials as Scaffolds for Electronic, Optical, Magnetic, Semiconducting, and Biotechnological Applications", published Aug. 4, 2005; (9) No. 2005-0180992 entitled "Viral Fibers", published Aug. 18, 2005; (10) No. 2005-0221083 entitled "Inorganic Nanowires", published Oct. 6, 2005; and (11) No. 2006-0121346 entitled "Virus Scaffold for Self-Assembled Flexible and Light Lithium Battery", published Jun. 8, 2006, each of which is incorporated herein by reference in its entirety. These references describe a variety of specific binding modifications which can be carried out for binding conjugate structures, as well as forming the conjugate structures in the presence of the material modified for specific binding. In particular, polypeptide and amino acid oligomeric sequences can be expressed on the surfaces of viral particles, including both at the ends and along the length of the elongated virus particle such as M13 bacteriophage, including pIII and pVIII expressions, as well as pIX, pVII, and pVI expressions, and combinations thereof.

In addition, the following paper by Whaley et al., "Selection of Peptides with Semiconductor Binding Specificity for Directed Nanocrystal Assembly", Nature, 2000, 405: 665-668 is also incorporated herein by reference. This paper shows a method of selecting peptides with binding specificity using a combinatorial library. Specifically, the paper shows a method of selecting peptides with binding specificity to semiconductor materials using a combinatorial library with about 109 different peptides. The combinatory library of random peptides, each containing 12 amino acids, were fused to the pIII coat protein of M13 coliphage and exposed to crystalline semiconductor structures. Peptides that bound to the semiconductor materials were eluted, amplified, and re-exposed to the semiconductor materials under more stringent conditions. After the fifth round of selection, the semiconductor specific phages were isolated and sequenced to determine the binding peptide. In this manner, peptides were selected with high binding specificity depending on the crystallographic structure and composition of the semiconductor material. The technique could be readily modified to obtain peptides with a binding specificity for not just semiconductor materials, but a range of both organic and inorganic materials.

In certain embodiments of the present invention, genetic programming is carried out to engineer a virus structure using different displayed peptide features of a virus such as the filamentous M13 virus. An overall advantage of this genetic programming approach to materials engineering, in addition to materials-specific addressability, is the potential to specify viral length and geometry. The length of the filamentous virus is generally related to the size of its packaged genetic information and the electrostatic balance between the pVIII-derived core of the virion and the DNA (see, for example, B. K. Kay et al., "*Phage Display of Peptides and Proteins: A Laboratory Manual*", Academic Press: San Diego, 1996). Phages observed by AFM generally are seen to be roughly 860 nm and as short as 560 nm depending on whether the complete M13 genome or smaller phagemid are used in sample preparation (see, for example, C. Mao et al., Proc. Natl. Acad. Sci., 2003, 100: 6946). Also, changing a single lysine to glutamine on the inner-end of pVIII can result in particles approximately 35% longer than wild-type phage (see, for example, J. Greenwood et al., J. Mol. Biol., 1991, 217:223).

II—Biomacromolecules

As already mentioned above, the present invention involves the formation of a two dimensional ordered monolayer biomacromolecules. Biomacromolecules suitable for use in the invention include any biomacromolecule that is charged (e.g., negatively charged) and can undergo spontaneous self-assembly according to methods of the present invention. The biomacromolecule can be naturally charged, or can be modified (e.g., synthetically transformed or genetically engineered) to carry a charge. In certain embodiments, the biomacromolecule has an elongated shape, e.g., a long, rod-like structure. In certain embodiments, the biomacromolecule has a rigid structure. In some embodiments, the biomacromolecule can be functionalized (e.g., mono or multi-functionalized). The functional group(s) can be recognition sites which provide sites for binding, nucleation, and/or catalysis.

Biomacromolecules suitable for use in the practice of the present invention can be found in a variety of classes of molecules including, but not limited to, proteins, polypeptides, polynucleotides, lipids, polysaccharides, filamentous proteins, peptide fibers, biopolymer fibers, viruses, and viruses particles. The molecular weight of the biomacromolecules can be anywhere between about 1,000 and about 100,000,000 grams/mole, preferably from about 10,000 to about 25,000,000 grams/mole.

Viruses

In certain embodiments of the present invention, the biomacromolecule is a virus (or virus particle). The virus is not particularly limited as long as it is charged (e.g., negatively charged) or can be modified to carry a charge (e.g., by genetic engineering). Preferably, the virus can be functionalized. In general, virus particles which are long, filamentous structures can be used in the practice of the present invention (see, for example, "*Genetically Engineered Viruses*", C. Ring (Ed.), Bios Scientific, 2001). Additionally, other viral geometries such as dodecahedral and icosahedral can be functionalized and used to create materials according to the present invention.

In certain preferred embodiments, the size and dimensions of the virus particles can be such that the particle is elongated. For example, the viral particles may have a cross sectional diameter of about 3 nm to about 20 nm and a length of about 60 nm to about 6,000 nm. More particularly, the length can be about 250 nm to about 2,000 nm, for example, about 500 nm, about 600 nm, about 700 nm, about 800 nm, about 900 nm, about 1000 nm, about 1,000 nm, about 1,200 nm, about 1500 nm, about 1700 nm or about 1900 nm. Generally, viruses suitable for use in the present invention may be characterized by an aspect ratio of at least 25, at least 50, at least 75, at least 100, or even at least 250 or 500.

In certain embodiments, the structure of the virus particles can be such that the particle has a rigid elongated configuration (i.e., the particle has a limited/restricted conformational flexibility and does not undergo significant folding and unfolding reactions). Steric constraints introduced by the rigidity of the virus reduce the ability to maximize charge-charge contacts between the virus and the positively-charged polyelectrolyte of the PEM and result in competitive exchange of the virus with the negatively-charged polyelectrolyte of the PEM (see below).

Virus particles suitable for use in the present invention can include an entire virus or portions of a virus comprising at least the virus capsid. As used herein, the term "virus" refers to both viruses and phages. Entire viruses can include a nucleic acid genome, a capsid, and may optionally include an envelop. Suitable viruses may further include both native and heterologous amino acid oligomers, such as cell adhesion factors. The nucleic acid genome may be either a native genome or an engineered genome. Virus particles may or may not contain DNA, and if virus particles do contain DNA, the DNA may or may not encode for the viral capsid. In general, a virus particle has a native structure, wherein the peptide and nucleic acid portions of the virus are configured in particular arrangement, that are sought to be preserved when it is converted to solid state, self-supporting forms such as films.

A wide variety of viruses may be used in the practice of the present invention. The inventive compositions and materials may comprise a plurality of viruses of a single type or a plurality of different types of viruses. In certain embodiments, the viruses are helical viruses. Examples of helical viruses include, but are not limited to, tobacco mosaic virus (TMV), phage pfl, phage fdl, CTX phage, and phage M13. These viruses are generally rod-shaped and may be rigid or flexible. In certain embodiments, rigid-rod shaped viruses are used. One skilled in the art may select viruses depending on the intended use of the final material and properties of the virus.

In certain embodiments, M13 systems are used as viruses in the present invention. The wild-type filamentous M13 virus is approximately 6.5 nm in diameter and 880 nm in length (N. K. Kay et al., "*Display of Peptides and Proteins: A Laboratory Manual*", Academic Press: San Diego, 1996). The length of the cylinder reflects the length of the packaged single-stranded DNA genome size. The capsid of M13 virus includes several proteins. At one end of the M13 virus, there are approximately five copies of each of pII and pIX proteins. The other end has about five copies of each of pIII and pVI proteins. The wild-type M13 virus coat includes about 2700 copies of major coat protein pVIII, which are stacked in units of five in a helical array. This unit periodic, uniform structure is genetically controlled.

Genetically Engineered Viruses

In certain embodiments, virus particles are used which are not genetically engineered. However, in general, desirable properties can be achieved when the virus is genetically engineered. For example, viruses can be used which have been subjected to biopanning so that the virus particles can specifically recognize and bind to the materials which is the object of the biopanning. The materials can also be nucleated and synthesized in particulate form, including nanoparticle form, in the presence of the specific recognition and binding sites. Use of filamentous viruses in so-celled directed evolution or biopanning is known in the art and has been described, for example, in U.S. Pat. Nos. 5,223,409 and 5,571,698, each of which is incorporated herein by reference.

In certain embodiments, viruses are used that have been engineered to express one or more peptide sequences, including amino acid oligomers, on the surface of the viruses. The amino acid oligomers may be native to the virus or heterologous sequences derived from other organisms or engineered to meet specific needs. The expression of the amino acid oligomers may serve a number of functions including, but not limited to, binding sites for organic or inorganic molecules or particles, nucleation sites for organic or inorganic molecules or particles. Expression of amino acid oligomers allows the viruses and materials comprising the viruses to be engineered to specific applications. For example, amino acid oligomers with specificity for an inorganic molecule may be expressed to bind or nucleate the inorganic molecule to increase the efficiency of a chemical reaction. In another example, the expressed amino acid oligomer may bind and detect an organic molecule (e.g., a biological warfare agent). Such material could be incorporated into the clothing of military personnel or first responders as part of a sensor system. These are only a few examples of the utility of materials comprising engineered viruses, and other applications will be readily apparent to one skilled in the art.

Amino acid oligomers may be of any length and may include non-amino acid components. Oligomers having about 5 to about 100, and more particularly about 5 to about 30 amino acid units as specific binding/nucleation sites can be used. Non-amino acid components include, but are not limited to, sugars, lipids, drugs, enzymes, or inorganic molecules, including electronic, semiconducting, magnetic, and optic materials.

Genetically engineered viruses can be prepared by methods and using vectors as described in, for example, N. K. Kay et al., "Display of Peptides and Proteins: A Laboratory Manual", Academic Press: San Diego, 1996, in particular Chapter 3 entitled "Vectors for Phage Display" and references cited therein. Alternatively or additionally, genetically engineered viruses can be prepared by methods as described for example, in Barbas et al., "Phage Display: A Laboratory Manual", 2001, including Chapter 2 entitled "Phage Display Vectors" and references cited therein. The type of vector is not particularly limited. Table 2.1 of the Barbas lists exemplary vectors that can be used in various combinations to provide multifunctional viruses. For example, type 3, type 8+8, and phagemid type p7/p9 can be combined. Or type 8 and type 3 can be combined along with phagemid type p7/p9 as desired. One skilled in the art can develop other combinations based on particular applications. Methods can be developed to either display the peptide on some or substantially all copies of the coat protein.

A number of other prior art references teach the engineering of viruses to express amino acid oligomers and may be used to assist in practicing the present invention. For example, U.S. Pat. No. 5,403,484 discloses the selection and expression of heterologous binding domains on the surface of viruses. U.S. Pat. No. 5,766,905 discloses a display vector comprising DNA encoding at least a portion of capsid protein followed by a cloning site for insertion of a foreign DNA sequence. The compositions described are useful in producing a virus expressing a protein or peptide of interest. U.S. Pat. No. 5,885,808 discloses an adenovirus and methods of modifying an adenovirus with a modified cell-binding moiety. U.S. Pat. No. 6,261,554 shows an engineered gene delivery vehicle comprising a gene of interest and a viral capsid or envelope carrying a member of a specific binding pair. U.S. published patent application No. 2001-0019820 shows viruses engineered to express ligands on their surface for the detection of molecules, such as polypeptides, cells, receptors, and channel proteins. See also U.S. published patent application No. 2005-0170336 to Belcher et al. for methods of engineering viruses to nucleate inorganic materials and form metallic, magnetic, or semiconductor materials.

In embodiments wherein M13 systems are used, the different regions, such as pIII, pVI, pVII, pVIII, and pIX, may express the same or different amino acid oligomers. For example, pIII and pVIII may express amino acid oligomers, with different binding or nucleating specificities. In addition, amino acid oligomers with different binding specificities may be expressed on the same region, such as pVIII. For example, glutamic acid and aspartic acid, which contain carboxylic acid side chains, may be genetically expressed on the pVIII protein and used to bind various metal ions via chelation (see, for example, U.S. published patent application No. 2006-0121346 to Belcher et al., which is incorporated herein by reference in its entirety). The ratio of glutamate to aspartate in the peptides may range from 100% glutamate to 100% aspartate. Alternatively or additionally, an inert peptide sequence may be coupled to the carboxylated peptide sequence, or a peptide that is selective for some other material may be coupled to the carboxylated peptide. The carboxylate enhancement may be expressed on all the pVIII chains (100% display) or may be partially displayed using various techniques for modifying bacteriophage genomes well known in the art. Alternatively or additionally, the carboxylate enhancement may be expressed on one of the other coat proteins (e.g., pIII).

The affinity of the desired metal or oxide for the modified virus may be optimized using the phage display library techniques described in U.S. published patent application No. 2003-0073104 published on Apr. 17, 2003, the contents of which are incorporated herein by reference. The use of phage display provides a method to co-locate both ionic and electronic conductors, which can be useful in the fabrication of batteries (e.g., lithium ion batteries). In certain embodiments, a peptide sequence that selectively binds an electronic conductor may be incorporated into the protein coat of the virus. For example, biopanning may be used to identify a peptide sequence that is selective for a desired catalyst, e.g., copper, gold, silver, nickel, platinum, palladium, etc. This peptide may be expressed on a different coat protein than the modified coat protein that binds the metal oxide. Alternatively or additionally, the peptide may be expressed on a portion of the same coat protein (e.g., pVIII) on which the peptide for the metal oxide is expressed. For example, biopanning using a library of variations in one coat protein may be used to identify a peptide sequence for which a polynucleotide is engineered such that the peptide is expressed in a different coat protein. The resulting virus, expressing one type or two types of modified peptides, may then be used to nucleate nanoparticles of the metal oxide, with or without an electronic conductor.

Conjugates

The conjugate material is not particularly limited. In general, it will be selected for a particular application. It can be selected so that the virus particles can be subjected to biopanning against the conjugate material, and then the conjugate material is selectively or specifically bound to the virus particle. In some applications, selective binding can be sufficient, whereas in other applications, a more powerful specific binding can be preferred. The virus can act as a catalyst for formation of or biomineralization of the conjugate material on the virus.

Examples of general types of conjugate materials include inorganic, organic, particulate, nanoparticulate, small molecule, single crystalline, polycrystalline, amorphous, metallic, noble metal, magnetic, semiconductor, polymeric, electronically conducting, optically active, conducting polymeric, light-emitting, phosphorescent, and fluorescent materials. Conjugate materials can be directly linked to the recognition site or can be linked to the recognition site by a linking moiety. Conjugate materials can be formed in the presence of the recognition moiety and coupled to it and bind to it as it is formed. Or, conjugation materials can be preformed and then bound to the recognition site. For example, nanocrystals can be nucleated at the recognition sites or can be preformed and bound to the recognition sites. Conjugate materials which are useful electrode materials such as, for example, noble metals and gold can be used. Conjugate materials are described further, for example, in the patent applications and technical literature to Angela Belcher and co-workers cited in this specification.

Conjugate materials can be, for example, preformed quantum dots such as those available from Quantum Dot Corp. Quantum dots can comprise a core-shell structure, where the core can be, for example, CdS, CdSe or CdTe, and the shell can be, for example, zinc sulfide. The quantum dots can also be subjected to a further coating such as a hydrophobic/hydrophilic polymer having carboxylic acid derivatization. The hydrophobic part can interact with the inorganic inside of the quantum dot, and the hydrophilic part can interact with the exterior including solvent. Examples of patents describing quantum dots include, for example, U.S. Pat. Nos. 6,322,901; 6,576,291; 6,423,551; 6,251,303; 6,319,426; 6,426,513; 6,444,143; 5,990,479; 6,207,392; 6,251,303; 6,319,426; 6,426,513; 6,444,143; 5,990,479; 6,207,392; 6,423,551; 6,251,303; 6,319,426; 6,426,513; 6,444,143; 5,990,479; 6,207,392; 5,990,479; 6,207,392; 6,423,551; 6,306,610; 6,326,144; 5,990,479; 6,207,392; 6,274,323; 6,207,392; 6,500,622; 6,815,064 and 6,649,138.

III. Polyelectrolytes for Multilayer Films

In the present invention, a two-dimensional monolayer structure of biomacromolecules is formed atop of a polyelectrolyte multilayer (PEM). PEM, used as a charge-mediating medium for monolayer assembly, has the advantage of enabling the delicate control of surface charge density by varying salt concentration or pH of polyelectrolyte solution, which allows facile processing conditions without any complicating equipment and procedure. Preferred PEMs suitable for use in the present invention are mobility-enhancing polyelectrolyte multilayers.

The oppositely charged polymers (i.e., polyelectrolytes) used for the PEM may be soluble in water and/or organic solvents. In certain preferred embodiments, the polyelectrolytes are water soluble.

Examples of polyelectrolytes that are soluble in water include poly(styrenesulfonic acid), poly(2-acrylamido-2-methyl-1-propane sulfonic acid), sulfonated lignin, poly(ethylenesulfonic acid), poly(methacryloxyethylsulfonic acid), poly(acrylic acids), poly(methacrylic acids) their salts, and copolymers thereof; as well as poly(diallyldimethyl-ammonium chloride), poly(vinylbenzyltrimethylammonium), ionenes, poly(acryloxyethyl-trimethyl ammonium chloride), poly(methacryloxy(2-hydroxy)propyl-trimethyl ammonium chloride), and copolymers thereof; and polyelectrolytes comprising a pyridinium group, such as, poly(N-methylvinylpyridium), protonated polyamines, such as, poly(allylamine hydrochloride) and poly(ethyleneimmine)

Examples of polyelectrolytes that are soluble in non-aqueous solvents, such as ethanol, methanol, dimethylformamide, acetonitrile, carbon tetrachloride, and methylene chloride include poly(N-alkylvinylpyridines) and poly(N-alkylvinylimidazoles), and copolymers thereof in which the alkyl group is longer than about 4 carbon atoms. Other examples of polyelectrolytes soluble in organic solvents include poly(styrenesulfonic acid), poly(diallyl-dimethylammonium chloride), poly(N-methylvinylpyridinium) and poly(ethyleneimine) where the small polymer counterion, such as chloride or bromide, has been replaced by a large hydrophobic counterion such as tetrabutyl ammonium, tetraethyl ammonium, iodine, hexafluorophosphate, tetrafluoroborate, or trifluoromethane sulfonate.

The polyelectrolytes generally comprise one or more monomer repeat units that are positively or negatively charged. The charge may be disposed in side groups pendant from the polymer backbone, may be attached to the backbone directly, or can be incorporated in the backbone itself. The polyelectrolytes may be copolymers that have a combination of charged and/or neutral monomers (e.g., positive and neutral; negative and neutral; positive and negative; or positive, negative and neutral). Regardless of the exact combination of charged and neutral monomers, a polyelectrolyte used in the present invention is predominantly positively charged or predominantly negatively charged and hereinafter is refer to as a "positively-charged polyelectrolyte" or a "negatively-charged polyelectrolyte" if the polymer carries a net positive charge or a net negative charge at neutral pH, respectively. Some polyelectrolytes comprise a repeat unit that has both a negative and positive charge. Such repeat units are termed "zwitterionic" and the polyelectrolyte is termed a "zwitterionic polyelectrolyte". Preferably, polyelectrolytes comprising zwitterionic groups also comprise pH sensitive units. These pH sensitive units can be acrylic acids, carboxylic acids, and copolymers thereof, and protonable nitrogens, such as pyridines, imidazoles, piperidines, and primary, secondary or tertiary amine groups such as allylamine. Zwitterionic groups can be present on polyelectrolytes as blocks or randomly dispersed throughout the polymer chain. Zwitterionic polyelectrolytes may be neutrally charged at one pH, positively charged at another pH, and negatively charged at a third pH.

The charges on a polyelectrolyte may be derived directly from the monomer units or they may be introduced by chemical reaction on a precursor polymer. Thus, for example, poly(styrenesulfonic acid) can be made by polymerizing the negatively charged styrene sulfonate monomer. It can also be made by sulfonation of neutral polystyrene. The chemical modification of precursor polymers to produce charged polymers may be incomplete and typically result in an average charge per repeat unit that is less than 1.

Negatively-charged polyelectrolytes may include carboxylate, sulfonate, sulfate, phosphate, nitrate, or other negatively charged or ionizable groups. Examples of negatively-charged synthetic polyelectrolytes suitable for use in the practice of the present invention and comprising sulfonate groups ($—SO_3^-$) include, but are not limited to, poly(styrenesulfonic acid) (PSS), poly(2-acrylamido-2-methyl-1-propane sulfonic acid) (PAMPS), sulfonated poly(ether ether ketone) (SPEEK), poly(ethylenesulfonic acid), poly(methacryloxyethylsulfonic acid), their salts, and copolymers thereof. Examples of negatively charged synthetic polyelectrolytes suitable for use in the practice of the present invention and comprising carboxylate groups include, but are not limited to, poly(acrylic acid) (PAA) and poly(methacrylic acid).

Positively-charged polyelectrolytes may include protonated amine, quaternary ammonium or phosphonium derived functions or other positively charged or ionizable groups. Examples of positively-charged synthetic polyelectrolytes suitable for use in the practice of the present invention and comprising a quaternary ammonium group include, but are not limited to, poly(diallyldimethylammonium chloride) (PDAC), poly(vinylbenzyl-trimethylammonium) (PVBTA), ionenes, poly(acryloxyethyl-trimethyl ammonium chloride), poly(methacryloxy(2-hydroxy)propyltrimethyl ammonium chloride), and copolymers thereof. Examples of positively charged polyelectrolytes comprising a pyridinium group include, but are not limited to, poly(N-methylvinylpyridinium) (PMVP), other poly(N-alkylvinylpyridines), and copolymers thereof. Examples of positively-charged polyelectrolytes comprising protonated polyamines include, but are not limited to, poly(allylaminehydrochloride) (PAH) and polyethyleneimines (PEI), e.g., linear polyethyleneimine (LPEI).

To induce a self-assembly, in general, there is a requirement of high mobility for assemblable species. In many embodiments of the present invention, reversible weak electrostatic interaction between charged entities is the essential source to induce the interdiffusion and resulting biomacromolecule (e.g., virus) mobility. Recent investigations have revealed that there can be a reversible interdiffusion within polyelectrolyte multilayer in some pairs of weak polyelectrolytes typically showing a characteristic of superlinear thickness growth (C. Picart et al., Proc. Natl. Acad. Sci. USA, 2002, 99: 12531-12535; P. Lavalle et al., Macromolecules, 2002, 35: 4458-4465). Accordingly, in certain preferred embodiments a pair of weak oppositely charged polyelectrolytes are used in the practice of the present invention. As already mentioned above, weak polyelectrolytes are polyelectrolytes that become charged at certain pH values. For example, poly(acrylic acids) and derivatives begin to take on a negative charge within the range of about pH 4 to about pH 6 and are negatively charged at higher pH levels. Below this transition pH range, however, poly(acrylic acids) are protonated (i.e., uncharged). Similarly, polyamines and derivatives take on a positive charge if the pH of the solution is below the $pK_a$. As such, and in accordance with the present invention, the pH of a polyelectrolyte solution may be adjusted by the addition of an acid and/or base in order to attain, maintain and/or adjust the electrical charge of a polyelectrolyte, or of a polyelectrolyte at the surface of, or within, a polyelectrolyte multilayer.

Examples of pairs of weak polyelectrolytes suitable for use in the practice of the present invention include, but are not limited to, linear polyethylene-imine/poly(styrenesulfonic acid) (LPEI/SPS), poly(diallyldimethyl-ammonium chloride)/poly(styrenesulfonic acid) (PDAC/SPS), poly(allylamine hydrochloride/poly(styrenesulfonic acid) (PAH/SPS), linear polyethylene-imine/poly(acrylic acid) (LPEI/PAA), poly(diallyldimethylammonium chloride)/poly(acrylic acid) (PDAC/PAA), and poly(styrenesulfonic acid)/poly(acrylic acid) (PAH/PAA). In certain embodiments, the pair of weak polyelectrolytes used in the practice of the present invention contains linear-polyethylenimine (LPEI; 25,000 $M_w$) that is widely accepted as a biocompatible positively charged polyelectrolyte, and polyacrylic acid (PAA; 90,000 $M_w$) for the anionic counter ion. The present Applicants have shown that the LPEI/PAA pair is a strong candidate for the interdiffusion behavior and also shows good film processibility owing to its ultraflat surface roughness during deposition (mean roughness less than 1 nm) (see Example 1).

In certain embodiments, the pair of weak polyelectrolytes is selected such that there is a large difference between the $pK_a$ values of the positively-charged polyelectrolyte and the negatively-charged polyelectrolyte. In other embodiments, the pair of weak polyelectrolytes is selected such that there is a small difference between the $pK_a$ values of the positively-charged polyelectrolyte and the negatively-charged polyelectrolyte.

The molecular weight (number average) of synthetic polyelectrolyte molecules suitable for use in the practice of the present invention is typically about 1,000 to about 5,000,000 grams/mole, preferably about 10,000 to about 1,000,000 grams/mole. The oppositely charged polyelectrolytes used in the formation of the multilayer film according to the present invention may have similar molecular weights. Alternatively, the positively charged polyelectrolyte may have a molecular weight that is higher or lower than the molecular weight of the negatively charged polyelectrolyte. In embodiments where the LPEI/PAA pair is used, the positively charged polyelectrolyte has a molecular weight that is about 3.5 times than the molecular weight of the anionic counter ion.

In certain preferred embodiments, one of the pair of polyelectrolyte molecules (e.g., the positively-charged polyelectrolyte if the biomacromolecule is negatively charged) has a molecular weight that enhances, promotes or otherwise allows mobility/interdiffusion of the polyelectrolyte within the PEM, thus allowing the spontaneous ordering process of the biomacromolecule during assembly. As shown by the Applicants (see Example 1), a polyelectrolyte with a high molecular weight will have a reduced mobility compared to a lower-molecular weight polyelectrolyte.

In certain embodiments, the two weak polyelectrolytes are selected such that one of the polyelectrolytes exhibits preferential charge binding with the oppositely charged polyelectrolyte of the pair as opposed to the charged biomacromolecules. Thus, the two weak polyelectrolytes may be selected such that their surface charge densities are similar to each other but different from (e.g., lower or higher than) the surface charge density of the biomacromolecule. According to the present invention, this mismatch in charge distribution between the positively-charge polyelectrolyte and the negatively-charged biomacromolecule results in competitive exchange of the biomacromolecule with the negatively-charged polyelectrolyte, which increases the surface concentration of the biomacromolecule (see below). In preferred embodiments, the surface charge density of the polyelectrolytes is higher than the surface charge density of the biomacromolecule. For example, the surface charge density of the polyelectrolytes may be 2 fold higher than the surface charge density of the biomacromolecule, at least about 2 fold higher, at least about 3 fold higher, at least about 4 fold higher or more than 4 fold higher.

In certain embodiments, one or both oppositely charged polyelectrolytes is/are non-degradable. Examples of non-degradable polyelectrolytes include, but are not limited to, poly (styrene sulfonate) (SPS), poly(acrylic acid) (PAA), linear poly(ethylene imine) (LPEI), poly(diallyldimethyl ammonium chloride) (PDAC), and poly(allylamine hydrochloride) (PAH).

In certain embodiments, one or both oppositely charged polyelectrolytes is/are biocompatible. In certain embodiments, one or both oppositely-charged polyelectrolytes is/are degradable (e.g., hydrolytically degradable, biodegradable, thermally degradable, and photolytically degradable). Hydrolytically degradable polymers known in the art include, for example, certain polyesters, polyanhydrides, polyorthoesters, polyphosphazenes, and polyphosphoesters. Biodegradable polymers known in the art include, for example, polyhydroxyacids, polypropylfumerates, polycaprolactones, polyamides, poly(amino acids), polyacetals, polyethers, biodegradable polycyanoacrylates, and biodegradable polyurethanes. Specific examples of biodegradable polymers include polylysine, poly(lactic acid) (PLA), poly(glycolic acid) (PGA), poly(caprolactone) (PCL), poly(lactide-co-glycolide) (PLG), poly(lactide-co-caprolactone) (PLC), and poly(glycolide-co-caprolactone) (PGC).

IV. Preparation Methods

Methods of preparation of constructs of the present invention involve using the electrostatic layer-by-layer (LBL) assembly technique an/or polyelectrolyte multilayer films prepared by LBL assembly. Polyelectrolyte multilayer formation using LBL proceeds by sequential addition of polycations and polyanions. Upon addition of a polycation to a negatively-charged surface, the polycation deposits on the surface, forming a thin polymer layer and reversing the surface charge. Similarly, a polyanion deposited on a positively charged surface forms a thin layer of polymer and leaves a negatively charged surface. Alternating exposure to polycations and polyanions generate polyelectrolyte thin multilayer nanostructures with a surface charge determined by the last polyelectrolyte added (Decher et al., Thin Solid Films, 1992, 210: 831-835; G. Decher, Science, 1997, 277: 1232-1237; F. Caruso et al., Science, 1998, 282: 1111-1114; and Z. Tang et al., Nature Mater., 2003, 2: 413-418). As already mentioned above, polyelectrolyte multilayer systems obtained using the conventional LBL assembly technique are generally considered random, kinetically frozen networks in which the mobility of polymer chains is significantly limited. Adsorption of a charged virus (i.e., biomacromolecule) monolayer within such systems would only generate irreversible charge binding and lead to a randomly stacked virus layer (see, for example, FIG. 2b).

The present invention is directed to an improved strategy for electrostatically-mediated self-assembly of charged macromolecules. In this strategy, electrostatic charge exchange and interlinking between small charged molecules (i.e., polyelectrolytes) in medium (hereafter called interdiffusion), induces the dynamic mobility of large macromolecules (e.g., biomacromolecules), and then leads the segregation of macromolecule with the medium and finally completes the monolayer assembly on the surface. Based on the understanding of enhanced mobility of macromolecules by charged medium, the present invention provides two methods of monolayer formation technique: one is an indirect method of assembly from layered mixture to phase-separated monolayer and the other is a direct assembly on the charged surface. The methods of the present invention allow the control of assembly density and directionality while maintaining the stability and functionality of the resulting thin film.

Compared to other kinds of electrostatic interactions based assembly techniques that only use the static charged binding, the inventive methods use the dynamic electrostaticity as a driving force that is induced by interdiffusion between charged species. Additionally, unlike the electrophoresis technique that uses external electrostaticity to drive the separation of charged mixtures, the segregation of macromolecule with medium and further monolayer assembly according to the present invention, are progressed spontaneously and internally regulated without any external electrostatic source. According to the present invention, the construction of a quantitatively scalable and functionally controllable macromolecular monolayer surface and its assembly properties can be easily tuned by varying the environmental electrostatic condition of charged species.

The use of polymer (polyelectrolyte of small body)-polymer (biomacromolecule of large body) interface in the inventive methods offers many advantages over the air-water interface of Langmuir-Blodgett monolayer (LBM) assembly technique. In particular, in the inventive methods there is no need of attaching a specific functionality for hydrophobicity or separability and the polymer-polymer interface can be easily manipulated by intrinsic charge properties of constituents. Furthermore, by modulating the functionality of polyelectrolytes, it is possible to achieve multicomponent monolayer stacking for a hierarchical structure. The ability of generating monolayer of inorganic nanowires in a quantitative and uniform way on a large area scale without any treatment or transfer process will be particularly useful in the fabrication of nanodevices Indirect Monolayer Assembly of Macromolecules by Floating Through PEM The first inventive method comprises steps of: providing a plurality of negatively charged biomacromolecules; providing a polyelectrolyte multilayer thin film produced by layer-by-layer assembly using a weak positively-charged polyelectrolyte and a weak negatively-charged polyelectrolyte, wherein the surface of the film is positively charged; contacting the surface of the film with the biomacromolecules to obtain a thin film comprising biomacromolecules electrostatically bound to its surface; and forming, on top of the obtained thin film, a second polyelectrolyte multilayer by layer-by-layer assembly using the weak positively-charged polyelectrolyte and the weak negatively-charged polyelectrolyte.

A scheme showing an embodiment of this first method of self-assembly is presented on FIG. 2a. This scheme shows the formation of a monolayer of M13 virus on a thin film of LPEI/PAA (linear-polyethylenimine/polyacrylic acid) multilayer. First, negatively charged M13 viruses are electrostatically bound to a thin layer of positively charged top surface of LPEI/PAA multilayer prepared from layer-by-layer deposition technique (e.g., on a silicon or glass substrate) (step 1 on FIG. 2a). Further deposition of LPEI/PAA on the existing virus layer and their reversible weak electrostatic binding induces the interdiffusion between virus particles and PEM and brings about viruses floating on the surface (step 2 on FIG. 2a). Finally, virus particles floating on the surface are spontaneously reordered to closely-packed viral monolayer due to their repulsive liquid-crystalline behavior (step 3 on FIG. 2b).

The ordering of "floating" viruses is entropically driven and electrostatically regulated. Generally, in solution of high concentrated viruses, liquid crystalline ordering such as smectic or nematic phase is induced by the entropic excluded-volume (depletion) effect because the interparticle potential is dominated only by "steric hard-rod repulsion". However, in the present case, electrostatic interaction between viruses and PEM additionally contributes to the entropic ordering process by compensating the overall repulsive charge between viruses. To maximize the entropy of virus and the electrostatic linking with underlying PEM, consequently, the system spontaneously selects non-overlapped monolayer structure as optimized ordering phase.

As used herein, the term "polyelectrolyte multilayer film" refers to a film having at least one bilayer deposited material, wherein the term "bilayer" refers to a structure comprising one layer of a positively-charged polyelectrolyte and one layer of a negatively-charged polyelectrolyte.

In certain embodiments of the present invention, the polyelectrolyte multilayer thin film has a thickness of less than about 50 nm, e.g., less than about 40 nm, less than about 30 nm, less than about 20 nm, or less than about 10 nm. In some embodiments, the polyelectrolyte multilayer thin film has a thickness of about 10 nm or less than 10 nm, e.g., 9 nm, 8 nm, 7 nm, 6 nm, 5 nm, 4 nm or less than 4 nm. In some embodiments, the polyelectrolyte multilayer thin film has a thickness that is in the same order of magnitude than the thickness of the elongated biomacromolecule. Thus, in embodiments wherein M13 viruses are used (thickness of about 7 nm), the polyelectrolyte multilayer thin film has preferably a thickness of less than about 10 nm.

Alternatively or additionally, the thickness of the polyelectrolyte multilayer thin film may be described in terms of number of bilayers. In certain embodiments, the polyelectrolyte multilayer thin film comprises less than 6 bilayers, e.g., 5.5 bilayers, 4.5 bilayers, 3.5 bilayers, 2.5 bilayers, or 1.5 bilayers.

Forming a second polyelectrolyte multilayer by layer-by-layer assembly using the weak positively-charged polyelectrolyte and the weak negatively-charged polyelectrolyte on top of the thin film comprising biomacromolecules electrostatically bound to its surface comprises steps of: contacting the surface of this thin film with the weak positively-charged polyelectrolyte; contacting the film thus obtained with the weak negatively-charged polyelectrolyte; and repeating these steps one or more times. Generally, the weak positively-charged polyelectrolyte and the weak negatively-charged polyelectrolyte are each in an aqueous solution. Contacting may be performed by depositing the solution of one polyelectrolyte on the surface of the film or by dipping the film into the polyelectrolyte solution.

In certain embodiments, the second polyelectrolyte multilayer is prepared under conditions similar to those used in the preparation of the polyelectrolyte multilayer thin film (e.g., substantially identical concentrations of weak negatively-charged and weak positively-charged polyelectrolytes, substantially identical pH values of the aqueous solutions of polyelectrolytes, substantially identical temperature, etc). In other embodiments, a different set of conditions is used in the preparation of the second polyelectrolyte multilayer.

In certain embodiments, the second polyelectrolyte multilayer has a thickness of less than about 20 nm, e.g., less than about 15 nm, less than about 10 nm or less than about 5 nm. For example, the second polyelectrolyte multilayer has a thickness of 12 nm, 11 nm, 10 nm, 9 nm, 8 nm, 7 nm, or less than 7 nm. In certain embodiments, the second polyelectrolyte multilayer comprises less than 6 bilayers, e.g., 5.5 bilayers, 4.5 bilayers, 3.5 bilayers, 2.5 bilayers, or 1.5 bilayers.

Direct Monolayer Assembly of Macromolecules on Charged PEM surface

The second method of the present invention comprises steps of: providing a plurality of negatively charged biomacromolecules; providing a polyelectrolyte multilayer film produced by layer-by-layer assembly using a weak positively-charged polyelectrolyte and a weak negatively-charged polyelectrolyte, wherein the film is thick and the surface of the film is positively charged; and contacting the surface of the thin with the biomacromolecules.

A scheme showing an embodiment of this second method of self-assembly is presented on FIG. 8. This scheme shows the formation of a monolayer of M13 virus on a thick film of LPEI/PAA (linear-polyethylenimine/polyacrylic acid) multilayer. For a monolayer formation in a direct way, relatively thick layers of LPEI/PAA are deposited on the substrate, and then the negatively charged M13 virus is simply applied on the positively charged surface. In this method, entropic positional selection of M13 viruses dominates the ordering process, which leads to the formation of close-packed virus monolayer on PEM surface that is the same than FIG. 2c. What makes this simplified procedure possible is the thickness of the underlying PEM layer. As mentioned above, achieving mobility of the macromolecules is the key to monolayer assembly. In the inventive indirect assembly method, several layers of underlying LPEI/PAA can only generate a thin PEM medium (less than 10 nm) for virus attachment. In that case, thickness is comparable to the dimensions of the virus (~7 nm thick), which makes it difficult to provide enough mobility to the virus for a monolayer formation. However, in the inventive direct assembly method, initially thick bilayers of LPEI/PAA (thicker than 50 nm) can generate an enhanced interdiffusion in PEM and provide a full mobility to the virus.

Thus, in preferred embodiments of the present invention, the polyelectrolyte multilayer film has a thickness of more than 50 nm, e.g., at least 50 nm, at least 60 nm, at least 70 nm, at least 80 nm, at least 90 nm, at least 100 nm or more than 100 nm, e.g., 150 nm, 200 nm, 250 nm, 300 nm, 500 nm, 750 nm or 1 μm.

Alternatively or additionally, the thickness of the polyelectrolyte multilayer thick film may be described in terms of number of bilayers. In certain embodiments, the polyelectrolyte multilayer thick film comprises more than 6 bilayers, e.g., 6.5 bilayers, 7.5 bilayers, 8.5 bilayers, 9.5 bilayers, 10.5 bilayers, 11.5 bilayers, 12.5 bilayers, 13.5 bilayers, 14.5 bilayers, 15.5 bilayers, 16.5 bilayers, 17.5 bilayers or more.

The starting polyelectrolyte multilayer film in the direct and indirect methods of self-assembly of the present invention is generally deposited on a substrate. Substrates can be two- or three-dimensional and can comprise a planar surface or can be shaped. A variety of materials can be used as substrates including, but not limited to, metals, e.g., gold, silver, platinum, and aluminum; metal-coated materials; metal oxides; plastics; ceramics; silicon; glasses; mica; graphite; hydrogels; and polymers such as polyamides, polyphosphazenes, polypropylfumarates, polyethers, polyacetals, polycyanoacrylates, polyurethanes, polycarbonates, polyanhydrides, polyorthoesters, polyhydroxyacids, polyacrylates, ethylene vinyl acetate polymers and other cellulose acetates, polystyrenes, poly(vinyl chloride), poly(vinyl fluoride), poly (vinyl imidazole), poly(vinyl alcohol), poly(ethylene terephthalate), polyesters, polyureas, polypropylene, polymethacrylate, polyethylene, poly(ethylene oxide)s and chlorosulphonated polyolefins; and combinations thereof. For example, a substrate of one material may be coated with a second material, or two materials may be combined to form a composite.

The polyelectrolyte multilayer film may cover the whole surface of the substrate, or, alternatively, the polyelectrolyte multilayer film may cover only a region of the substrate.

As will be apparent to one skilled in the art, using methods provided herein, numbers of biomacromolecule monolayers and polyelectrolyte multilayers can be stacked alternatively.

Control of Monolayer Properties: Assembly Density and Directionality

In the methods of the present invention, the step of contacting the surface of the polyelectrolyte multilayer film with a plurality of negatively-charged biomacromolecules is carried out by depositing an aqueous solution of biomacromolecules to the surface. Assembly density may be controlled by varying the pH of the aqueous solution of biomacromolecules.

For example, the M13 virus has an intrinsic negative charge, which leads to mutual repulsion in solution, this electrostaticity may be modulated by varying the pH of the solution. Zeta potential measurements of M13 virus, as presented on FIG. 4a, have showed that there is a dramatic potential change in function of pH in the range between pH 4 and pH 6. The M13 virus has a slight positive charge around pH 4;

becomes negatively-charged above pH 4.3 and the change in the zeta potential increases rapidly until pH 5.3. Above pH 5.3, the zeta potential increases very slowly and nearly saturates. This potential change readily affects the monolayer assembly in its packing density. As the virus is more highly charged, the repulsion between viruses gets much stronger, which leads to a wider spacing between them in the self-assembly monolayer. A series of AFM images of M13 virus assembly presented on FIGS. 4b-d show that assembly density can be controlled by varying the pH Virus has a slight positive charge around pH 4.0, but is switched to negative above pH 4.3 and rapidly charged to strong until pH 5.3. Above that value, zeta potential increases very slowly and nearly saturates. This potential change readily affects the monolayer assembly of M13 virus in its packing density. As the virus is more highly charged, the repulsion between viruses gets much stronger, which leads to a wider spacing between them. A series of AFM images of virus assembly from FIG. 5 shows that assembly density can be controlled by varying the pH in the range from 4.8 to 5.5 to obtain assembly densities ranging from 1 to 100 viruses/$\mu m^2$.

Accordingly, in certain embodiments, the pH of the aqueous solution of the negatively-charged biomacromolecules is selected such that strong repulsion takes place between the negatively-charged biomacromolecules. In such embodiments, a sparse monolayer of biomacromolecules is obtained. In other embodiments, the pH of the aqueous solution of the negatively-charged biomacromolecules is selected such that weak repulsion takes place between the negatively-charged biomacromolecules. In such embodiments, a dense and highly ordered monolayer of biomacromolecule is obtained. It is within the skill in the art to select a pH for a given biomacromolecule to modulate the degree of electrostatic repulsion between the molecules. In the case of the direct method of self-assembly, the pH of the aqueous solutions of the negatively-charged polyelectrolyte and/or of the positively-charged polyelectrolyte may identical to the pH of the aqueous solution of biomacromolecules.

Alternatively or additionally, the biomacromolecules may be genetically engineered to manipulate (e.g., increase or decrease) the surface charge density of the biomacromolecule. Increased surface charge density leads to increased repulsion between the biomacromolecules and therefore sparse monolayer formation, while decreased surface charge density leads to decreased repulsion and therefore dense monolayer formation.

Mobility of biomacromolecules is also affected by temperature as diffusion is a thermally activated process. Furthermore, the ordering of a monolayer is driven entropically, by the exclusion of volume. Therefore, the ordering factor and assembly density is dependent on temperature. Higher temperature provides more driving force, resulting in highly ordered and dense monolayer.

Accordingly, in certain embodiments, the method of self-assembly is performed at a temperature that increases the electrostatic repulsion of the negatively-charged biomacromolecules. In such embodiments, a sparse monolayer of biomacromolecules is obtained. In other embodiments, the method of self-assembly is performed at a temperature that decreases the electrostatic repulsion of the negatively-charged biomacromolecules. In such embodiments, a dense monolayer of biomacromolecules is obtained. The dimension of the ordering is not limited. Depending on the substrate, it can reach a few meters.

Another aspect of controllability for the formation of biomacromolecule monolayer is a directional ordering. Directionality can be realized by flowing the biomacromolecule solution in a microfluidic channel. Such a microfluidic channel has been used in the formation of a M13 virus monolayer. As shown on FIG. 9, directionally ordered virus monolayer of nematic phase was obtained.

As already mentioned above, further mineralization and nanoparticle binding from a two dimensionally ordered biomacromolecule scaffold prepared according to methods of the present invention enables the assembly of dense, highly ordered and nanostrutured hybrid monolayer.

V—Uses

As already mentioned above, functional thin films prepared according to the present invention can be used in many different commercial applications, some of which are noted above, including the cited patents, patent applications and references. The functional thin films can be used, for example, in applications requiring electrical conductivity or semi-conductivity at the nanoscale. The large surface area to volume ratio of the inventive systems is advantageous for applications, such as, fuel cells, thin film batteries, and supercapacitors. As already mentioned, the surface of the thin film can be modified, doped, or otherwise modified in its material structure for the application. Microcircuitry, nanocircuitry, macroelectronics, photovoltaics, solar cells, chemical and biological sensors, optical components, field emitting tips and devices, nanocomputing, nanoswitches, molecular wire crossbars, batteries, fuel cells, catalysts, very large flat panel displays, tiny radio frequency identification devices, smart cards, phased array RF antennas, disposable computing and storage electronics, nanoscale bar codes, cross bar nanostructures, biosensor arrays, high density data storage, field effect transistors, and the like are representative examples of applications for the nanowires. Particularly important semiconductive elements include, for example, p-n diodes, p-i-n diodes, LEDs, and bipolar transistors. Thin films can be incorporated into a number of devices, such as electronic, optoelectronic, electrochemical, and electromechanical devices.

Additional applications of the inventive functional thin films will be readily apparent to one skilled in the art.

EXAMPLES

The following examples describe some of the preferred modes of making and practicing the present invention. However, it should be understood that these examples are for illustrative purposes only and are not meant to limit the scope of the invention. Furthermore, unless the description in an Example is presented in the past tense, the text, like the rest of the specification, is not intended to suggest that experiments were actually performed or data were actually obtained.

Some of the results presented in this section have been described by the Applicants in recent scientific publications (P. L. Yoo et al., Nature Mater., 2006, 5: 234-240; K. T. Nam et al., Science, 2006, 312: 885-888), each of which is incorporated herein by reference in its entirety.

Example 1

Spontaneous Assembly of M13 Viruses on Multilayered Polymer Surfaces

Introduction

Electrostatic interactions of repulsion and attraction that are ubiquitous in nature can be used to induce molecular mobility for ordering of nanoscopic to macroscopic systems, exemplified by separations as demonstrated in electrophoresis, or organization as in biomolecular self-assembly. In the present study, electrostatically induced interdiffusion between weakly charged polyelectrolytes drives the separation and two-dimensional (2D) liquid-crystal ordering of virus particles (M13 viruses) during alternating electrostatic assembly with complementary polyelectrolytes. In addition, because the genome of the M13 virus is easy to manipulate, the virus can be coded to grow and assemble specific inorganic materials, thus forming an ordered array of self-assembling nanowires.

The electrostatic layer-by-layer (LBL) assembly technique allows the adsorption of multiply charged species to create nanometer-scale films that form an effective ionically crosslinked network (G. Decher, Science, 1997, 277: 1232-1237; F. Caruso et al., Science, 1998, 282: 1111-1114; and Z. Tang et al., Nature Mater., 2003, 2: 413-418). The use of the LBL technique enables the creation of ultrathin functional films and highly tunable surfaces through the control of electrostatic interactions; the assembly process has the added advantage of strong compatibility with biomolecular species without loss of biological function. The Applicants chose this assembly process as a mean of incorporating genetically engineered M13 virus particles to create cohesive thin films, thus allowing the coupling of virus functionality and thin-film characteristics such as conductivity, electrochemistry, and biodegradability, depending on the choice of polyion (P. T. Hammond, Adv. Mater., 2004, 16: 1271-1293). Although such multilayer systems are generally considered random, kinetically frozen networks, the complete rearrangement of the films examined here can be induced through interdiffusion of polyelectrolytes during adsorption. Remarkably, the competitive interdiffusion that usually leads to disorder and disruption in electrostatically assembled thin films is harnessed to achieve spontaneous ordering of virus particles during the assembly process; this finding is particularly surprising given the high-molecular weight nature of the M13 viral macromolecule (about 14,000,000 $M_w$).

Linear-polyethylenimine (LPEI, 25,000 $M_w$), which is widely accepted as a biocompatible polymer (C. S. De Smedt et al., Pharm. Res., 2000, 17: 113-126), was used as the polycationic building block, and anionic polyacrylic acid (PAA, 90,000 $M_w$) was used as a counter-ion (D. M. DeLongchamp and P. T. Hammond, Chem. Mater., 2003, 15: 1165-1173). Investigations have revealed that reversible interdiffusion can take place within LBL assemblies consisting of certain pairs of weak polyelectrolytes; such multilayers typically show the characteristic of superlinear growth (C. Picart et al., Proc. Natl. Acad. Sci. USA, 2002, 99: 12531-12535; P. Lavalle et al., Macromolecules, 2002, 35: 4458-4465). The present Applicants have found that the LPEI/PAA polyelectrolyte pair was a strong candidate for this interdiffusion behavior (FIG. 1a), and also showed good film processibility owing to its ultraflat surface roughness during deposition (mean roughness less than 1 nm).

Figure 1B:
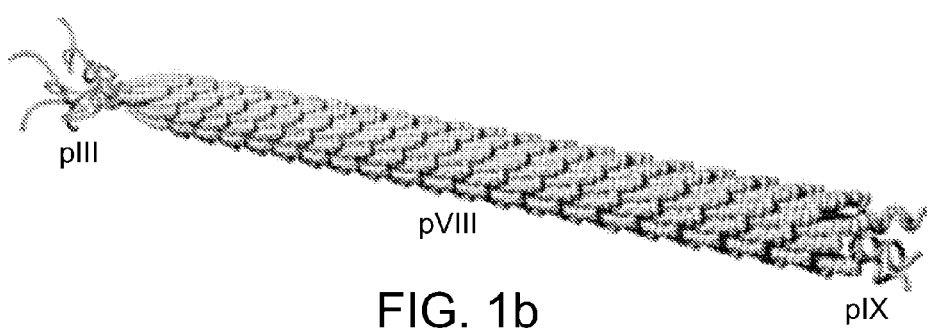
FIG. 1(b) is a schematic presentation of the engineered M13 virus and its functional groups as used in Example 1. The proteins at pIII in the head group and pVIII around the capsid body of the virus can be genetically engineered to have specific function(s) with biological or inorganic materials. The virus structure was constructed from the crystal structure of p8 protein (Protein Data Base No.: 1ifj).
Figure 3A:
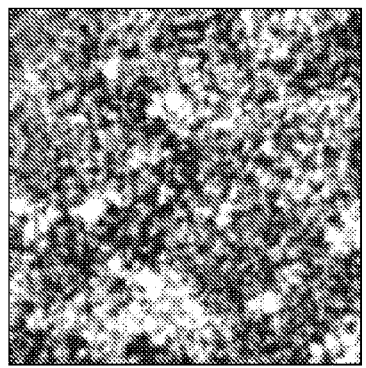
FIG. 3 shows a series of images taken to investigate the interdiffusion process in the LPEI/PAA system (see Example 1). The $1.5 \times 1.5$ $\mu m^2$ height-mode AFM images are presented (Z-range, height scale, 20 nm). All of the species are deposited at pH 5.0. a, Initial disorderly adsorbed viruses on $(LPEI/PAA)_{3.5}$. b-e, Alternating depositions of LPEI and PAA onto the prepared virus layer of a. f, After further deposition of $(LPEI/PAA)_{4.5}$ onto the surface of e. A highly ordered and closely packed monolayer of M13 virus is obtained on the surface. The scale bar in a refers to all parts.
Figure 3B:
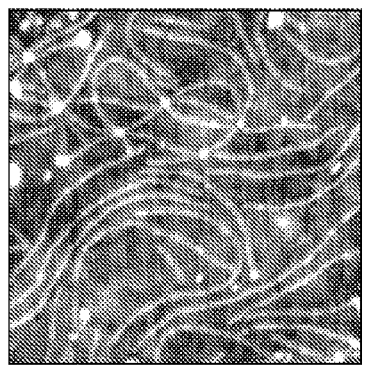
Figure 3C:
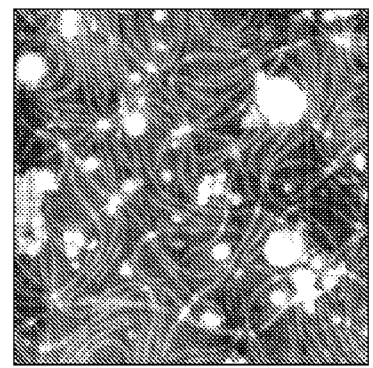
Figure 3D:
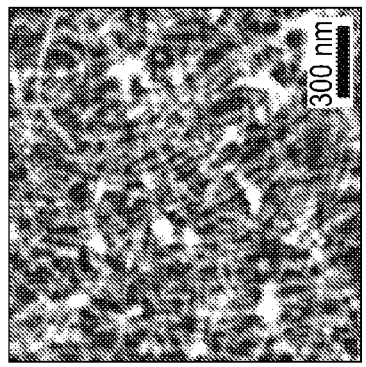
Figure 3E:
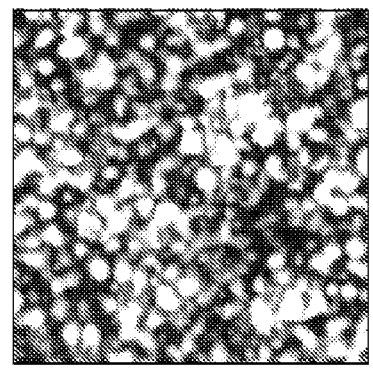
Figure 3F:
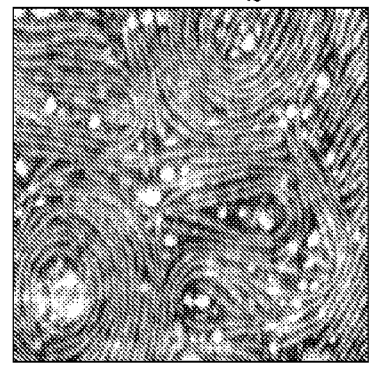

The M13 virus is a filamentous and negatively charged virus (M. Adams et al., Nature, 1998, Nature, 393: 349-352). The inherent monodispersity and anisotropic nature of the M13 virus inspired the Applicants to extend their successful realization of a three-dimensional liquid-crystal solution at high concentration to a large-area 2D thin-film surface assembly. In addition, the different locations of proteins (FIG. 1b, pIII and pVIII coat) on viruses and programmable protein functionalities by genetic engineering make viral systems an attractive toolkit for synthesis and assembly of nanoparticles and nanowires (S. W. Lee et al., Science, 2002, 296: 892-895; C. Mao et al., Science, 2004, 303: 213-217). In particular, the advances in modifying the major coat protein of the virus facilitate peptide interactions with inorganic ions for further biomineralization, as well as the control of the surface charge density of the virus (Y. Huang et al., Nano Lett., 2005, 5: 1429-1434).

Materials and Methods

Layer-by-Layer (LBL) Film Assembly. LPEI (25,000 $M_w$ and 250,000 $M_w$) (Polysciences) and PAA (90,000 $M_w$, 25% aqueous solution (Polysciences) were used as-received and prepared as 0.02 M solutions based on the repeat-unit molecular weight in Milli-Q water. The pH of the LPEI and PAA solutions of weakly charged polyelectrolytes were adjusted to 5.0. LPEI/PAA multilayer thin films were made by the conventional LBL method by using an HMS programmable slide stainer (Zeiss). In a typical film assembly, 3.5-5.5 bilayers of LPEI/PAA were applied on the silicon substrate. In order to make a free-standing film (FIG. 5a), 80.5-100.5 bilayers of LPEI/PAA were prepared on the Teflon-AF (DuPont)-coated silicon substrate.

M13 Virus Assembly. The viruses were placed in water to give a diluted concentration ($10^{10}$ phages/mL) and the solution pH was adjusted by adding 0.01 M HCl or 0.01 M NaOH. Then, 1 mL of the virus solution was dropped on the prepared LBL films of LPEI/PAA (2 cm×4 cm). After incubation for 30 minutes, the virus-assembled film was rinsed with Milli-Q water and dried by blowing with nitrogen.

M13 Virus Engineering. A pVIII library was constructed by fusing eight random amino acids into the N terminus of all the 2,700 copies of the pVIII proteins. It provided a random population of $10^7$-$10^8$. Through the use of a general biopanning technique by exposing the pVIII libraries to GaN, the peptide sequences that have a binding affinity for GaN were evolved and identified. After each round of selection and washing, the tightly bound phage clones were eluted with low pH and amplified using bacterial medium (*Escherichia coli* strain ER2738, New England Biolabs).

Surface Characterization. The virus-ordered surface was characterized with AFM (Digital Instruments, Dimension 3100) in tapping mode at an amplitude set point of 0.8 V under dry conditions. In order to obtain high-resolution images, supersharp silicon probes (Pacific Nanotechnology, SSS-NCH) were used to capture the image. Height and phase images were taken at scanning rates of approximately 1.5 Hz.

Results

The interdiffusion-induced viral assembly process is schematically depicted in FIG. 2a. Negatively charged M13 viruses were randomly deposited on the positively charged top surface of very thin LPEI/PAA multilayers (less than 10 nm) by electrostatic interactions (step 1). The PAA which has stronger electrostatic interactions with LPEI, competes with the virus macromolecule, driving a separation process that forces the virus to the surface (step 2). Finally, mutually repulsive interactions due to the liquid-crystalline behavior between virus molecules induce a spontaneous ordering process on the surface that results in an ordered viral monolayer structure (step 3, FIG. 2c). Some aspects of this process have analogies, interestingly to Langmuir-Blodgett assembly techniques, which are driven by hydrophobic interactions (D. Whang et al., Nano Lett., 2003, 3: 1255-1259; P. Yang, Nature, 2003, 425: 243-244). However, the use of the polyelectrolyte-biomacromolecule interface used in the present study offers many advantages over techniques exploiting air-water interfaces. In particular, because the viruses are easily manipulated at the DNA level to produce the desired chemical functionality, there is no need to attach a specific functionality for hydrophobicity, charge or segregation. Simple modifications in the DNA sequence allows to manipulate the intrinsic charge properties of the constituents, which yields an additional degree of tunability in this system. In addition, the LBL adsorption process has been shown to be easily scalable up to meter length scales, in contrast to the more difficult manipulation of materials at liquid-air interfaces. In conventional polyelectrolyte multilayer (PEM) systems, strong charge binding between ion pairs yields an ionically crosslinked network in which the mobility of polymer chains is significantly limited, in such cases, the intermixing or diffusion of polyions (C. Picard et al., Proc Natl. Acad. Sci. USA, 2002, 99: 12531-12535) within the interior of the PEM film during multilayer construction is not facilitated. Adsorption of a charged virus monolayer within such a system would only generate irreversible charge binding and lead to a randomly stacked virus layer (FIG. 2b). When one of the polyelectrolytes is able to interdiffuse into the multilayer, however, it is possible to "unlock" these electrostatic cross-links through competitive interactions.

To investigate this interdiffusion and ordering process, the present Applicants have monitored the buildup process for a series of polyelectrolytes atop an already adsorbed viral stack (FIG. 3). A thin base polyelectrolyte multilayer (less than 5 nm thick) was first deposited onto a silicon substrate; onto this multilayer, viruses were directly adsorbed from a dilute buffer solution. Finally, LPEI and PAA were alternately adsorbed on top of the viral layer using the same adsorption conditions as for the base layer, and the topography of the thin film was monitored systematically with increasing deposition number using tapping-mode atomic force microscopy (AFM). It is clear that the originally adsorbed viral layer is highly disordered (FIG. 3a). When the first LPEI layer is deposited atop these viruses, it appears that some of the viruses are able to diffuse to the surface through the top LPEI layer (FIG. 3b). In contrast, counter-ionic PAA deposition completely blankets the virus particles, resulting in a structure in which the viruses are buried under the surface (FIG. 3c). This process implies that LPEI plays a key role in driving the interdiffusion. It appears that it diffuses underneath the virus layer and into the multilayer matrix during LPEI deposition, and diffuses outwards to the overlying virus-covered surface layer, hence forming globular complexes with PAA during PAA deposition from solution. Accordingly, when LPEI is once again adsorbed, interdiffusion and complexation exchange processes between LPEI and PAA chains both at the surface and throughout the interior of the film take place, leading to the freeing of more viral particles from the original adsorbed layer within the film. This alternating process of preferential complexation, displacement of viruses and repeated deposition of polyelectrolyte increases the surface concentration of the virus, driven by competitive electrostatic interactions (FIG. 3d,e). Interestingly, after each deposition, the number of "floating" viruses freed from the PEM matrix and accumulated at the surface is increased, and the size of the PAA globules becomes larger after each PAA adsorption step because the number of free chains of LPEI that can participate in the interdiffusion process increases, yielding an exponentially growing thin film (P. Lavalle et al., Macromolecules, 2002, 35: 4458-4465). Finally after deposition of additional layers, the viruses form a close-packed monolayer (FIG. 3f).

Stepwise AFM observations indicate that LPEI is the mobile species within the film that drives the interdiffusion through its preferential binding with PAA compared with the virus coat. More importantly, it enables the direct visualization of the interdiffusion process within the PEM down to the nanometer-thickness regime. In this case, the viruses act as effective tagging agents, which can be compared to the conventional fluorescence labelling and confocal microscopy technique relevant to micrometer-scale systems (C. Picard et al., Proc Natl. Acad. Sci. USA, 2002, 99: 12531-12535). In separate ongoing work, the present Applicants have shown, using dye-conjugated LPEI, that LPEI can undergo interdiffusion during the adsorption process in the construction of LPEI/PAA multilayer thin films. The reasons for preferential charge binding with PAA as opposed to the negatively charged viral coats might be considered due to differences in charge density and chain conformation. At approximately pH 5, the charge density of the capsid body of the M13 virus (1-1.5 $e^-$ per subunit, where $e^-$ is an electron, K. R. Purdy and S. Fraden, Phys. Rev., 2004, E70, 061703; K Zimmermann et al., J. Biol. Chem., 1996, 261: 1653-1655) is lower than the surface charge density of LPEI (3-4 $e^-$ $nm^{-1}$, R. Meszaros et al., Langmuir, 2002, 18: 6164-6169). This mismatch in charge distribution between LPEI and the virus molecules, as well as steric constraints introduced by the rigidity of the virus that restrict the ability to maximize charge-charge contacts, result in competitive exchange of the virus with PAA. To test the concept of LPEI as the mobile species, and to examine the impact of molecular chain size on interdiffusion based on polymer dynamics using the generalized reptative polymer chain model (T. P. Russell et al., Nature, 1993, 365: 235-237), the Applicants replace the LPEI used in the above experiments with LPEI with a molecular weight ten times higher (250,000 $M_w$). The reduced mobility of the larger-molecular weight LPEI species resulted in the effective blocking of chain interdiffusion by LPEI within the PEM, and thus the virus could not effectively undergo the spontaneous ordering process during assembly.

Figure 4A:
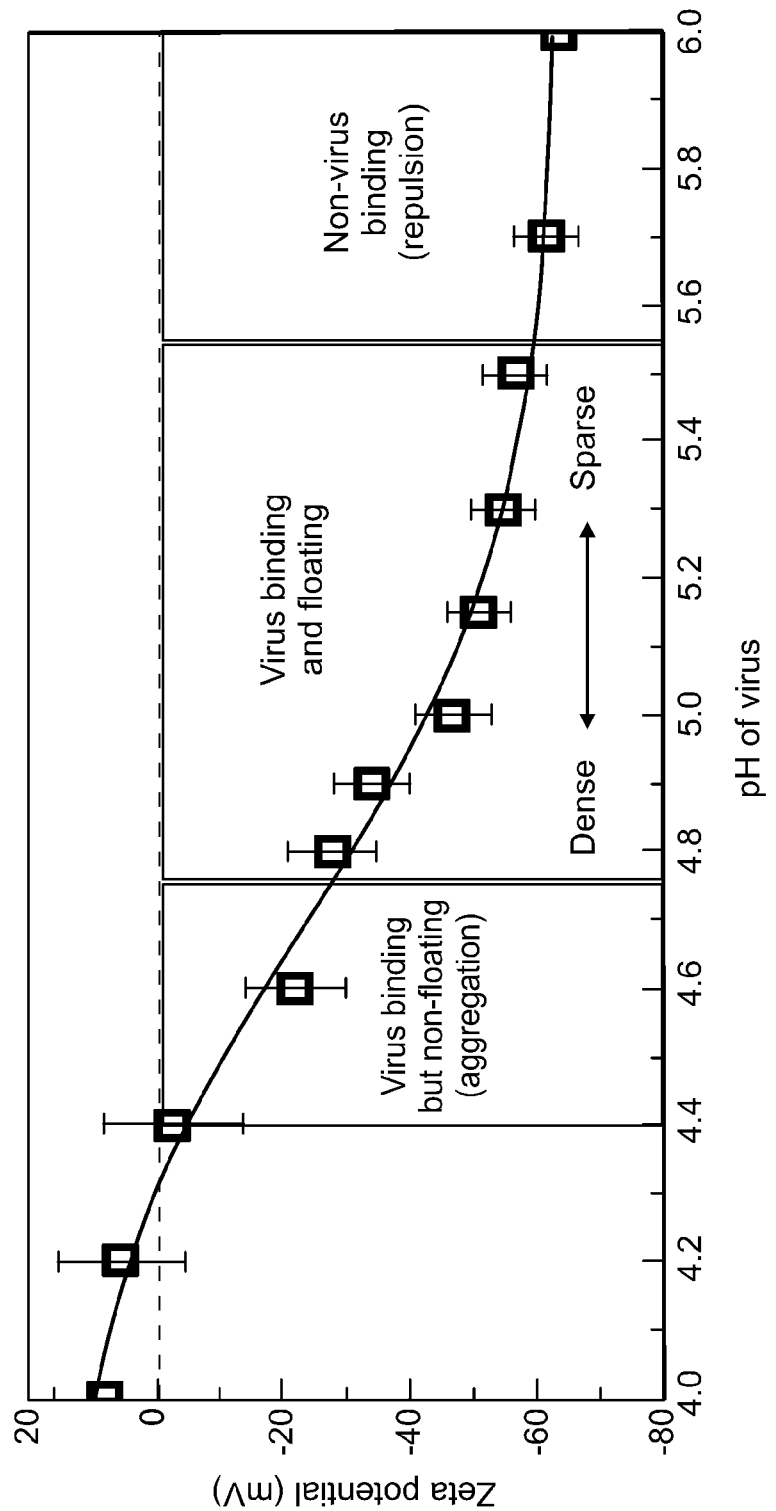
FIG. 4 shows results of density control in an electrostatically regulated viral monolayer (see Example 1). a, Zeta potential-pH dependence of the M13 virus and a brief description of the assembly behavior of the floated virus on top of the PEM. Each point of potential value was obtained by averaging 10 measurements, and error bars indicate standard deviations. b-d, Phase-mode AFM images of size $1.0 \times 1.0$ $\mu m^2$ (Z-range, $30°$). $(LPEI/PAA)_n$ was deposited at pH 5.0 and viruses were adsorbed at different pH values. Densely close-packed structures as shown in b (pH 4.8, 60 viruses $\mu m^2$), loosely packed structures as in c (pH 5.15, 25 viruses $\mu m^2$) and sparsely ordered structures as in d (pH 5.5, 10 viruses $\mu m^2$) can be obtained because stronger repulsive interactions at higher pH result in fewer adsorbed viruses. The scale bar in b refers to all parts.

The mesophase ordering of the viruses at the top surface is entropically driven and electrostatically regulated. Generally, in solutions of highly concentrated viruses, liquid-crystalline ordering such as smectic or nematic phases are induced by the entropic excluded-volume (depletion) effect because the interparticle potential is dominated only by "steric hard-rod repulsion" (M. Adams et al., Nature, 1998, 393: 349-352; J. Herzfeld, Acc. Chem. Res., 1996, 29: 31-37; Z. Dogic and S. Fraden, Phys. Rev. Lett., 1997, 78: 2417-2420). However, in the present case, electrostatic interactions between the viruses and the PEM (polyelectrolyte multilayer) also contribute to the entropic ordering process by compensating or shielding the overall repulsive charge between viruses. Similar ordering processes for charged species were reported experimentally in the ordered complexation of DNA/liposome systems by X-ray scattering analysis (J. O. Radler et al., Science, 1997, 275: 810-814), and theoretically in the responsive liquid-crystal behavior of actin filaments in the cytoskeleton (I. Borukhov et al., Proc. Natl. Acad. Sci. USA, 2005, 102: 3673-3678). To maximize the entropic state of the viruses and their electrostatic attractions with the underlying PEM, the virus molecules arrange in non-overlapping, close-packed-monolayer structures with optimized order. The random initiation and non-directional propagation of ordering ultimately leaves topological defects (FIGS. 2c and 3f) (H. R. Brand et al., Macromolecules, 1992, 25: 7223-7226). The typical singularity defects of liquid-crystal disclinations were observed: Mobius defects of strength s=±½ and spiral defects of s=±1. The removal of these ordering defects and unidirectional orientation of the viruses by application of an external shear force is also being investigated. The major coat protein sequence (pVIII) of the virus and the pH of the virus solution can manipulate the surface charge of M13 virus, determining the assembly behavior. Marked potential changes of the virus within a narrow pH region (FIG. 4a) enable to control the initial number of disordered adsorbed viruses, which results in final ordering densities ranging from 1 to 100 viruses $\mu m^2$ (FIG. 4b-d). Inorganic crystal nucleation or nanoparticle binding from the two-dimensionally ordered virus scaffold enables the assembly of dense, highly ordered and nanostructured hybrid monolayers even on free-standing polymer films (FIG. 5a), which is a prerequisite for the realization of practical devices in nano-electronics, magnetics and optics.

To illustrate the versatility of this system, the Applicants have assembled nanowire monolayers that were composed of a noble metal, a transition metal and semiconductor material. Three strategies were used for the formation of these nanowire arrays. The first was utilization of the electrostatic interactions for binding cationic nanoparticles to a negatively charged virus layer. The second involved peptide-mediated biomineralization of metal ions. The third involved phage selected from a 100% display library for a peptide sequence on the viral coat that was specific to bind to GaN. So far, biomolecular scaffolds such as DNA, lipids and proteins have been used to fabricate nanowires or arrays of nanoparticles (M. G. Warner et al., Nature Mater., 2003, 2: 272-277; S. Mann et al., Science, 1993, 261: 1286-1292; M. M. Murr and D. E. Morse, Proc. Natl. Acad. Sci. USA, 2005, 102: 11657-11662), which act as individual building blocks. However, the potential of these systems is limited in part owing to difficulties in organizing the individual blocks over large length scales, and limitations in the variety of inorganic materials that can be used.

FIG. 5b shows that 5-nm cationic gold nanoparticles were arrayed along the M13 virus scaffold when the virus scaffold was modified to express a tetraglutamate sequence as an amino acid (N) terminal protein fusion (pVIII). The same tetraglutamate M13 virus was used to nucleate cobalt nanowires by incubation of cobalt ions with the two-dimensionally ordered virus scaffold, followed by reduction with $NaBH_4$ (FIG. 5c). The carboxylic acid side chain of glutamic acid is capable of binding positive cobalt ions by an ion exchange mechanism. To form GaN monolayers (FIG. 5d), the Applicants used the method of phage selection from a random octamer peptide display pVIII library. The Applicants have previously shown that M13 phage virus display can be used to specifically bind nanobiological materials (S. W. Lee et al., Science, 2002, 296: 892-895 and S. R. Whaley et al., Nature, 2000, 405: 665-668, which are incorporated herein by reference). A solution of GaN nanoparticles was incubated with GaN specific phage in a two-dimensionally ordered array resulting in a densely packed film of GaN wires. The GaN virus nanowire film was imaged with AFM and maintains the fluorescent properties of the GaN nanoparticles.

An advantage of this method is that it can provide a tool for the construction of quantitatively scalable and functionally controllable biomolecular surfaces on this flexible polymer film. The film thickness can be varied for example, from 10 nm to tens of micrometers. In addition, the polyelectrolyte multilayer film can be doped with a broad range of materials, from conducting and redox-active polymers to biologically compatible materials. The flexibility, variety of inorganic materials that can grow and the low cost of synthesis and assembly of these materials systems will enable many potential technological applications, including chemical and biological sensors, power devices and catalytic reactive membranes. Applications that the present Applicants are currently investigating include the synthesis and assembly of thin-film electrode materials on ionically conductive multilayers to construct light-weight, flexible, lithium batteries, solar cells, and light-emitting diodes.

Example 2

Two-Dimensional Assembly of Viruses on Polyelectrolyte Multilayers for Thin, Flexible Lithium Ion Batteries There is an increasing need for smaller and flexible Li ion batteries and for methods to assemble battery materials. Nanoparticles, nanotubes (A. S. Claye et al., J. Electrochem. Soc., 2000, 147: 2845; J. S. Sakamoto and B. Dunn, J. Electrochem. Soc., 2002, 149: A26) and nanowires (A. R. Armstrong et al., Adv. Mater., 2005, 17: 862), as well as several assembly methods, using lithography, block copolymer (S. C. Mui et al., J. Electrochem. Soc., 2002, 149: A1610), or layer-by-layer deposition (T. Cassagneau and J. H. Fendler, Adv. Mater., 1998, 10: 877), have been introduced for constructing dimensionally small batteries. In addition to their utility in nanoelectronics, there is also growing evidence that nanostructured materials can improve the electrochemical properties of Li ion batteries compared to their bulk counterparts (A. S. Arico et al., Nature Mater., 2005, 4: 366). However, in order to attain this maximum potential, monodisperse, homogeneous nanomaterials and hierarchical organization control are needed. Bio-systems inherently have the molecular recognition and the capability of self-assembly, thus are attractive template for constructing and organizing the nanostructure (S. Mann, "*Biomineralization: Principles and Concepts in Bioinorganic Materials Chemistry*", Oxford University Press: New York, 2001; A. M. Belcher et al., Nature, 1996, 381: 56; M. M. Murr and D. E. Morse, Proc. Natl. Acad. Sci. USA, 2005, 102: 11657; N. C. Seeman, Nature, 2003, 421: 427; S. Brown, Nat. Biotechnol., 1997, 15: 269; T. Douglas and M. Young, Nature, 1998, 393: 152; and S Zhang, Nat. Biotechnol., 2003, 21: 1171). The Applicants have previously used viruses to assemble semiconductor and magnetic nanowires (C. Mao et al., Science, 2004, 303: 213; C. Mao et al., Proc. Natl. Acad. Sci. USA, 203, 100: 6946) and consider whether they can be used for device fabrication. Using batteries as example device, the present Applicants have explored whether the viruses can be modified to improve the electrode materials. As the viruses can assemble on multiple length scales, there may be scope for designing hierarchical self-assembling batteries. For this biological approach, once the genes are programmed for a functional device, very little past synthesis processing is necessary. Additionally, this biological route uses room-temperature, aqueous synthesis conditions.

Figure 6:
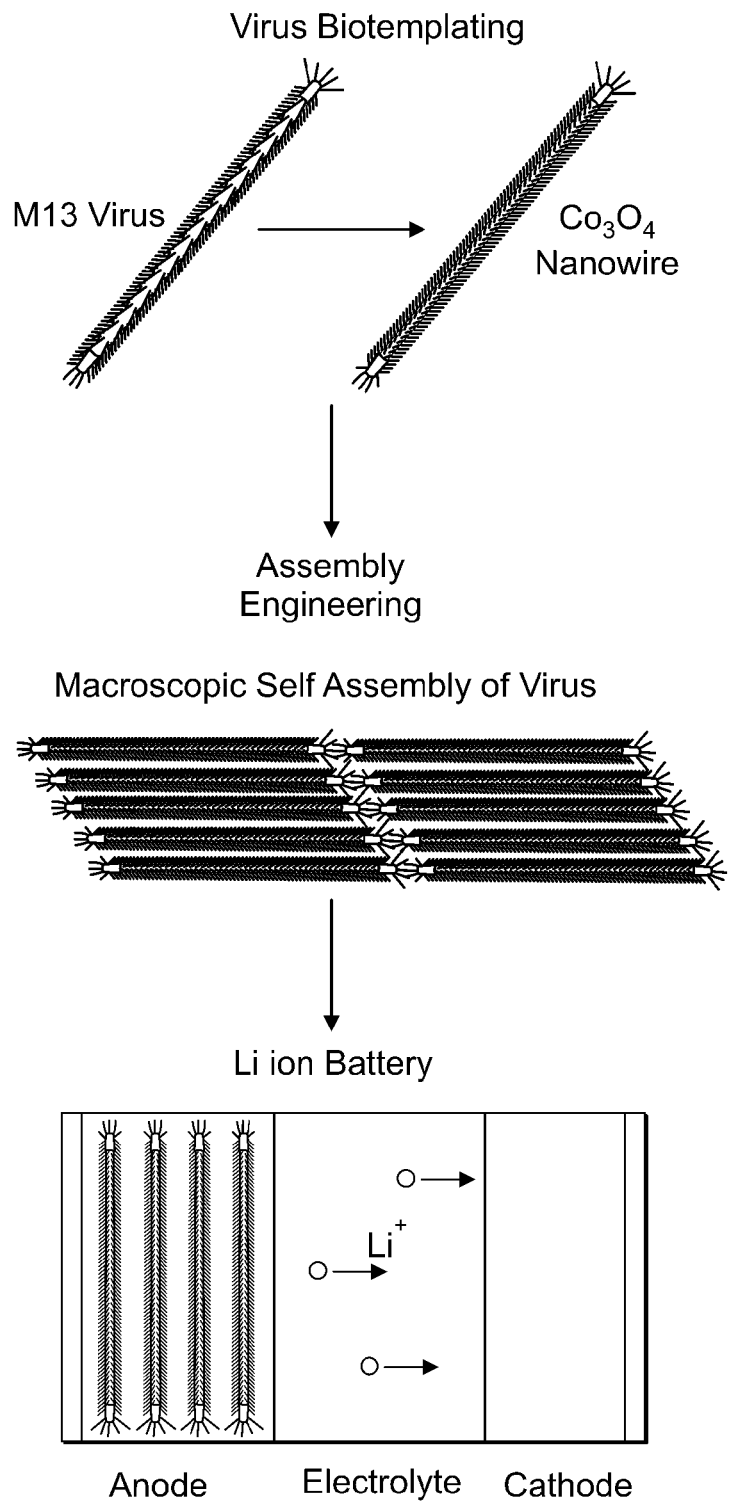
FIG. 6 shows a schematic diagram of a virus enabled synthesis and assembly of nanowires as negative electrode materials for lithium ion batteries according to one embodiment of the present invention (see Example 2). Rationally designed peptide and/or materials specific peptides identified by biopanning were expressed on the major coat pVIII proteins of M13 viruses to grow $Co_3O_4$ and $Au/Co_3O_4$ nanowires. Macroscopic ordering of the engineered viruses was utilized for fabricating an assembled monolayer of $Co_3O_4$ nanowires for flexible, light weight Li ion batteries.

Predictive based design was used for engineering the virus to satisfy the multifunctional purpose of electrode formation and assembly with a polymer electrolyte for the Li ion battery (FIG. 6). Tetra-glutamate (EEEE-) was fused to the N-terminus of each copy of the major coat pVIII protein with one hundred percent expression. This clone, named E4 clone, was designed with three distinct purposes. First, it can serve as a general template for growing nanowires through the interaction of the glutamate with various metal ions (Virus Biotemplating in FIG. 6). Carboxylic acid, the side chain of glutamate, binds positive metal ions via ion exchange, as demonstrated in polymeric templates (S. Joly et al., Langmuir, 2000, 16: 1354). Glutamate is also believed to be important in biomineralization, as evident in its role in specific proteins that regulate the nucleation of biomaterials in nature. Second, tetra-glutamate acts as a blocking motif for gold nanoparticles (B. R. Peelle et al., Langmuir, 2005, 21: 6929), due to the electrostatic repulsion. Therefore, tetra-glutamate reduces non-specific gold nanoparticle binding to phage, thereby increasing the specificity of a gold specific peptide to bind gold in low concentration. Lastly, the E4 clone is ideally suited for electrostatically driven assembly with a charged polymer (Assembly Engineering in FIG. 6). E4 is more negatively charged than wild type virus, enabling a favorable interaction with the positively charged electrolyte polymer. Zeta potential measurements of the E4 clone reveal a dramatic potential change between pH 4.5 and pH 5.5, thus enabling a certain degree of charge control.

Figure 7A:
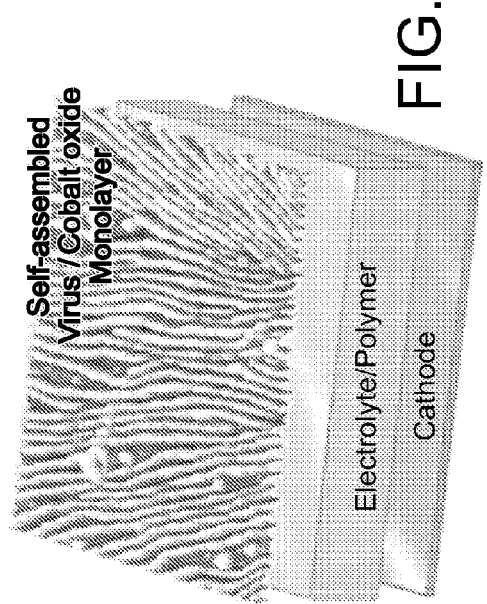
FIG. 7 shows results of two-dimensional assembly of $Co_3O_4$ nanowires driven by liquid crystalline ordering of engineered M13 bacteriophage viruses (see Example 2). (A) and (B) Phase mode AFM images of macroscopically ordered monolayer of $Co_3O_4$ coated viruses. Z-range is $30°$. (C) Digital camera image of a flexible and transparent free standing film of $(LPEI/PAA)_{100.5}$ on which $Co_3O_4$ viral nanowires are assembled into nanostructured monolayer with dimensions of 10 cm×4 cm. (D) Capacity for the assembled monolayer of $Co_3O_4$ nanowires/Li cell at two different charging rates.
Figure 7B:
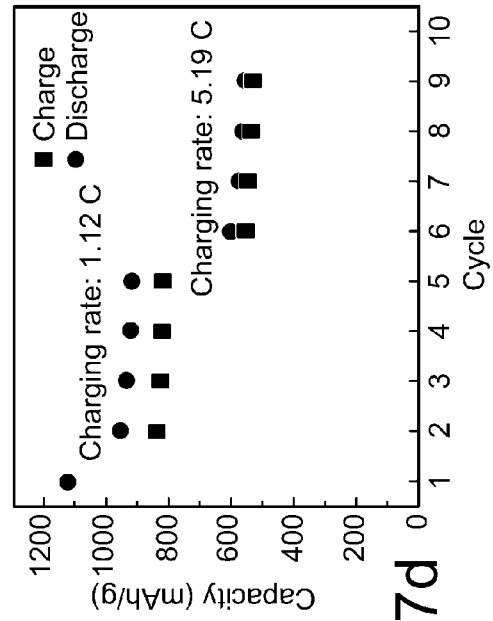
Figure 7C:
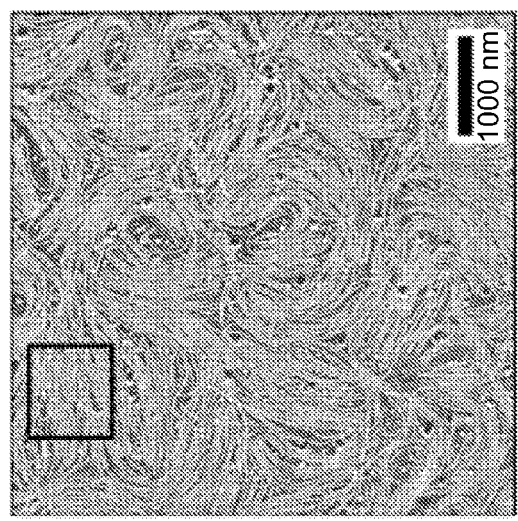
Figure 7D:
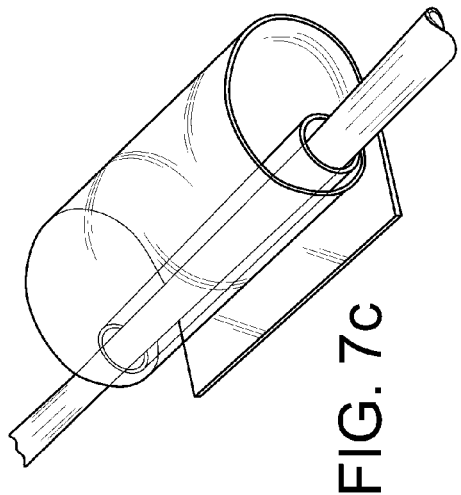

As shown above, the present Applicants have observed that negatively charged M13 viruses can form very ordered, two dimensional liquid crystalline layers on top of electrostatically cohesive films of LPEI/PAA. The ordering of engineered viruses is driven by competitive electrostatic interactions, the interdiffusion of the polyelectrolyte, and the anisotropic shape of M13 viruses. By employing this technique to spontaneously order E4 viruses and subsequently grow $Co_3O_4$ on the virus coat proteins, two dimensional organized ensembles of nanowires were produced on a 10 cm length scale (FIGS. 7A and 7B). The spatial distance and ordering behavior between viral nanowires can be manipulated by controlling both surface charge and fluidic forces. Furthermore, the thickness of the multilayered polymer can be varied from 10 nm to several micrometers independent of the substrate. This assembly process produced light weight, flexible, and transparent material/substrate multilayers, constructed as free standing films by a simple dipping method (FIG. 7C). This process should be scalable using roll-to-roll processing. Moreover, the polymer electrolyte is believed to act as a solid electrolyte because of the relatively fast ionic conductivity of LPEI and PAA pairs (D. M. DeLongchamp and P. T. Hammond, Chem. Mater., 203, 15: 1165: P. T. Hammond, Adv. Mater., 2004, 16: 1271-1293). Thus, the assembled layers comprise a negative electrode material grown upon a solid electrolyte or separator membrane. For electrochemical evaluation, 100 nm of Cu, which functions as a current collector, was deposited by E-beam evaporation on the assembled $Co_3O_4$ nanowires/polymer layer. This assembly was then tested in Swagelok™ cells using a Li foil negative electrode separated from the multilayer by a liquid electrolyte dipped separator (To prevent the oxidation of Cu after deposition of Cu in vacuum, the sample was rapidly transferred to a glove box for the assembly of the battery. In fact the contribution of CuO in charging/discharging curve was not observed. The mass of cobalt oxide on the polymer is 22 g/cm² measured by ICPMS). FIG. 7D shows the capacity for the assembled monolayer of $Co_3O_4$ nanowires/Li cell at two different charging rates. The cell was found to sustain and deliver 94% of its theoretical capacity at a rate of 1.12 C and 65% at a rate of 5.19 C, demonstrating the capability for high cycling rate. The power of the cell could be increased by alternating stacks of nanowire monolayers and polymer monolayers of LPEI and PAA or other polyions. In addition, Au—$Co_3O_4$ hybrid nanowires should also increase the total capacity.

The genetic approach presented for exploiting biomolecular interactions and self-assembly at various length scales has technological potential in the development of electrodes for nanostructured devices. The present results demonstrate that these traditionally biological principles can be utilized for the rational design and assembly of nanoscale battery components, exhibiting improved performance in properties such as specific capacity and rate capability. The genetic control in the viral synthesis of monodisperse oxide nanowires and the nanoarchitecture of hybrid nanowires can be advanced through further modification of other proteins. Heterostructured nanowires, comprising anode and solid electrolyte, and bio-energy transducing nanowires, coupled with biomolecules, are currently being investigated. Moreover, the self-organized virus monolayers for the generation of anodic as well as cathodic materials on ionically conducting polyelectrolyte films may present potential architectures for interdigitated batteries (J. W. Long et al., Chem. Rev., 2004, 104: 4463). The ease of genetic modification allows for the growth and assembly of other functional nanomaterials for further application such as photovoltaic devices, high surface area catalyst and supercapacitor.

OTHER EMBODIMENTS

Other embodiments of the invention will be apparent to those skilled in the art from a consideration of the specification or practice of the invention disclosed herein. It is intended that the specification and examples be considered as exemplary only, with the true scope of the invention being indicated by the following claims.

What is claimed is:

1. A composition comprising:
   a polyelectrolyte multilayer film, wherein the polyelectrolyte multilayer film comprises a positively-charged polyelectrolyte and a negatively-charged polyelectrolyte; and
   a plurality of biomacromolecules, which biomacromolecules are charged and can undergo spontaneous self-assembly, wherein, in the composition, the plurality of biomacromolecules are arranged in an ordered two-dimensional monolayer on a top surface of the polyelectrolyte multilayer film and contact a single polyelectrolyte multilayer film,
   wherein the ordered two-dimensional monolayer is a directionally ordered monolayer formed by flowing a solution including the plurality of biomacromolecules in a microfluidic channel.

2. The composition of claim 1, wherein the biomacromolecules are selected from the group consisting of proteins, polynucleotides, lipids, polysaccharides, and viruses.

3. The composition of claim 1, wherein the plurality of biomacromolecules comprises a virus.

4. The composition of claim 3, wherein the virus is a rod-shaped virus.

5. The composition of claim 4, wherein the virus is a rigid rod-shaped virus.

6. The composition of claim 4, wherein the virus has a cross-sectional diameter of about 3 nm to about 20 nm and a length of about 60 nm to about 6,000 nm.

7. The composition of claim 3, wherein the virus comprises at least one recognition site capable of a selective binding to or nucleating of a conjugate moiety.

8. The composition of claim 7, wherein the virus comprises a first recognition site capable of a first selective binding to or nucleating of a first conjugate moiety, and a second recognition site located differently from the first recognition site capable of a second selective binding to or nucleating of a second conjugate moiety.

9. The composition of claim 8, wherein the virus further comprises a third recognition site located differently from the first and second recognition sites capable of a third selective binding to or nucleating of a third conjugate moiety.

10. The composition of claim 7, wherein the virus has been genetically engineered to comprise the at least one recognition site.

11. The composition of claim 10, wherein the recognition site comprises an expressed protein, peptide or peptide oligomer.

12. The composition of claim 7, wherein the conjugate moiety is a member of the group consisting of an inorganic material, an organic material, and a biomolecular material.

13. The composition of claim 7, wherein the conjugate moiety comprises a semiconductor, metallic, magnetic, polymeric, particulate, nanoparticulate, single crystalline, polycrystalline, amorphous, electronically conducting, optically active, conducting polymeric, light-emitting, phosphorescent, fluorescent, glass or ceramic moiety.

14. The composition of claim 1, wherein the plurality of biomacromolecules are all identical.

15. The composition of claim 1, wherein the plurality of biomacromolecules comprise different biomacromolecules.

16. The composition of claim 1, wherein the plurality of biomacromolecules are densely packed in the ordered two-dimensional monolayer.

17. The composition of claim 1, wherein the plurality of biomacromolecules are sparsely packed in the ordered two-dimensional monolayer.

18. The composition of claim 1, wherein the two dimensional monolayer of biomacromolecules has a density of about 1 to about 100 biomacromolecules/$\mu m^2$.

19. The composite of claim 1, wherein the positively-charged polyelectrolyte is a weak positively-charged polyelectrolyte.

20. The composite of claim 1, wherein the negatively-charged polyelectrolyte is a weak negatively-charged polyelectrolyte.

21. The composition of claim 1, wherein the positively-charged polyelectrolyte is a weak positively-charged polyelectrolyte and the negatively-charged polyelectrolyte is a weak negatively-charged polyelectrolyte, and they form a pair of weak oppositely charged polyelectrolytes.

22. The composition of claim 21, wherein the polyelectrolytes have a surface charge density that is higher than the surface charge density of the biomacromolecules.

23. The composition of claim 1, wherein the positively-charged polyelectrolyte and/or the negatively-charged polyelectrolyte is/are biocompatible.

24. The composition of claim 1, wherein the positively-charged polyelectrolyte and/or the negatively-charged polyelectrolyte is/are degradable.

25. A method of preparing the composition of claim 1, the method comprising the steps of:
providing the plurality of biomacromolecules;
providing the polyelectrolyte multilayer film produced by layer-by-layer assembly using the positively-charged polyelectrolyte and the negatively-charged polyelectrolyte, wherein the top surface of the film is positively charged; and
contacting the top surface of the film with the plurality of biomacromolecules by flowing the solution including the plurality of biomacromolecules in the microfluidic channel.

26. The method of claim 25, wherein the solution including the plurality of biomacromolecules is an aqueous solution.

27. The method of claim 26, wherein the aqueous solution including the plurality of biomacromolecules has a pH that is selected such that strong repulsion takes place between the biomacromolecules.

28. The method of claim 26, wherein the aqueous solution including the plurality of biomacromolecules has a pH that is selected such that weak repulsion takes place between the biomacromolecules.

29. The composition of claim 1, wherein a density of the ordered two-dimensional monolayer increases with an increase in a pH of a polyelectrolyte solution.

* * * * *